(12) United States Patent
Ueno et al.

(10) Patent No.: US 6,194,608 B1
(45) Date of Patent: Feb. 27, 2001

(54) PROCESS FOR SEPARATING AND PURIFYING ALKALI METAL SALTS OF HYDROXYNAPHTHALENECARBOXYLIC ACIDS

(75) Inventors: Ryuzo Ueno, Nishinomiya; Masaya Kitayama, Takarazuka; Kuniyo Yanagawase, Ibaraki; Yoshiro Uchiyama, Sanda; Shigeji Mori, Itami, all of (JP)

(73) Assignee: Kabushiki Kaisha Veno Seiyaku Oyo Kenkyujo, Osaka (JP)

( * ) Notice: Subject to any disclaimer, the term of this patent is extended or adjusted under 35 U.S.C. 154(b) by 0 days.

(21) Appl. No.: 09/194,019
(22) PCT Filed: Mar. 19, 1998
(86) PCT No.: PCT/JP98/01167
  § 371 Date: Nov. 19, 1998
  § 102(e) Date: Nov. 19, 1998
(87) PCT Pub. No.: WO98/42651
  PCT Pub. Date: Jan. 10, 1998

(30) Foreign Application Priority Data

Mar. 21, 1997 (JP) .................................................. 9-067823

(51) Int. Cl.$^7$ ...................................................... C07C 63/34
(52) U.S. Cl. .............................................................. 562/467
(58) Field of Search ............................................... 562/467

(56) References Cited

U.S. PATENT DOCUMENTS 4,916,257  *  4/1990  von Plessen et al. .
5,081,263  *  1/1992  von Plessen et al. .

* cited by examiner

*Primary Examiner*—Paul J. Killos
(74) *Attorney, Agent, or Firm*—Sughrue, Mion, Zinn, Macpeak & Seas, PLLC

(57) ABSTRACT

The present invention provides a process for separating and purifying alkali metal salts of hydroxynaphthalenecarboxylic acids, in which alkali metal salt(s) of hydroxynaphthalenecarboxylic acid(s) are separated and purified from a mixture of alkali metal salts of hydroxynaphthalenecarboxylic acids by treating it with a nonionic porous synthetic adsorbent using water or water and water-soluble organic solvent(s).

5 Claims, 38 Drawing Sheets

● proportion of BON6-K (%)   ★ proportion of BON3-K (%)

● proportion of BON6-K (%)   ★ proportion of BON3-K (%)

● proportion of BON6-K (%)   ★ proportion of BON3-K (%)

● proportion of BON6-K (%) ★ proportion of BON3-K (%)

◆ recovery of BON6 (%) ★ recovery of BON3 (%) ☐ recovery of BON3, 6 (%)

● proportion of BON6 (%)  ★ proportion of BON3 (%)  ✷ proportion of BON3, 6 (%)

◆ recovery of BON6 (%)  ▲ recovery of BON3 (%)  ☐ recovery of BON3, 6 (%)

PROCESS FOR SEPARATING AND PURIFYING ALKALI METAL SALTS OF HYDROXYNAPHTHALENECARBOXYLIC ACIDS

TECHNICAL FIELD

The present invention relates to a process for separating and purifying alkali metal salts of hydroxynaphthalenecarboxylic acids.

BACKGROUND OF THE INVENTION

Hydroxynaphthalenecarboxylic acids are industrially produced by Kolbe-Schmitt process using naphthols converted to the alkali metal salts. The resultant products are obtained as a mixture of alkali metal salts of unreacted materiel and various hydroxynaphthalenecarboxylic acids having carboxyl groups at different positions. For example, 2-hydroxynaphthalene-3-carboxylic acid (hereinafter referred to as BON3) is obtained as a major component in the reaction products, when the sodium salt of 2-naphthol is used in the preparation of hydroxynaphthalenecarboxylic acids from 2-naphthol by Kolbe-Schmitt process. In contrast, 2-hydroxynaphthalene-6-carboxylic acid (hereinafter referred to as BON6) is obtained as a major component in the reaction products when the potassium salt of 2-naphthol is used in such preparation, although the potassium salt yields BON3 as a major component in the reaction products when reacted under high pressure. Other products such as 2-hydroxynaphthalene-3,6-dicarboxylic acid (hereinafter referred to as BON3,6) are also included in the reaction mixture.

Such hydroxynaphthalenecarboxylic acids are useful for various purposes. For example, BON6 is an important raw material for aromatic polyesters, and in particular, is an indispensable component for producing liquid crystal polymers having superior workability and high fluidity as well as resins or fibers having high elastic modulus and highly heat-resistant. BON3 and BON3,6 are also useful as raw materials for azo pigments. Similarly, alkali metal salts of hydroxynaphthalenecarboxylic acids are also useful as such. For example, the sodium salt of BON3 as such is useful as a raw material for azo pigments. The technique for separating and purifying such components from the reaction mixture is therefore quite important.

Several methods are already known for separating and purifying an intended compound from such mixtures, including, for example, those methods in which hydrochloric or sulfuric acid is added to adjust the pH in a predetermined range and thereby precipitate the intended compound or impurities, or in which the product is recrystallized using solvents (Japanese Patent Publication No. H1-216955, A (1989)), or in which the product is separated as an adduct with dioxane (Japanese Patent Publication No. H2-15046, A (1990)). Such methods, however, are not always preferred for industrial purpose because they involve a step in which alkali metal salts of hydroxynaphthalenecarboxylic acids produced are neutralized.

Disclosure of Invention

The present invention aims to separate and purify an intended compound(s) at an extremely high separation accuracy from a mixture of alkali metal salts of hydroxynaphthalenecarboxylic acids, in particular, from a mixture of alkali metal salts of 2-hydroxynaphthalene-3-carboxylic acid and 2-hydroxynaphthalene-6-carboxylic acid, without going through any completely-neutralizing step.

The present invention relates to a process for separating and purifying alkali metal salts of hydroxynapbthalenecarboxylic acids, characterized in that a mixture of alkali metal salts of hydroxynaphthalenecarboxylic acids are adsorbed to a nonionic porous synthetic adsorbent, and treated with water or water and water-soluble organic solvent(s).

The present invention further relates to the above process for separating and purifying alkali metal salts of hydroxynaphthalenecarboxylic acids, in which the nonionic porous synthetic adsorbent is an aromatic copolymer mainly composed of styrene and divinylbenzene or a methacrylic copolymer mainly composed of monomethacrylate and dimethacrylate.

The alkali metal salts of hydroxynaphthalenecarboxylic acids in the present invention are preferably those salts in the form of carboxylates.

The present invention particularly relates to the above process for separating and purifying alkali metal salts of hydroxynaphthalenecarboxylic acids, in which the mixture of alkali metal salts of hydroxynaphthalenecarboxylic acids is dissolved in water or water and water-soluble organic solvent(s), injected into the top of an column packed with a nonionic porous synthetic adsorbent, developed firstly with water or water-soluble organic solvent(s) having a high water content and then with increased proportion(s) of water-soluble organic solvent(s) in the developer.

The process of the present invention enables separation and purification of intended alkali metal salt(s) of hydroxynaphthalenecarboxylic acid(s) at high accuracy and at high yield from a mixture of alkali metal salts of hydroxynaphthalenecarboxylic acids, such as those obtained in Kolbe-Schmitt process, without neutralizing them completely, and thereby improves the productivity of such industrial processes.

BEST MODE FOR CARRYING OUT THE INVENTION

Figure 1:
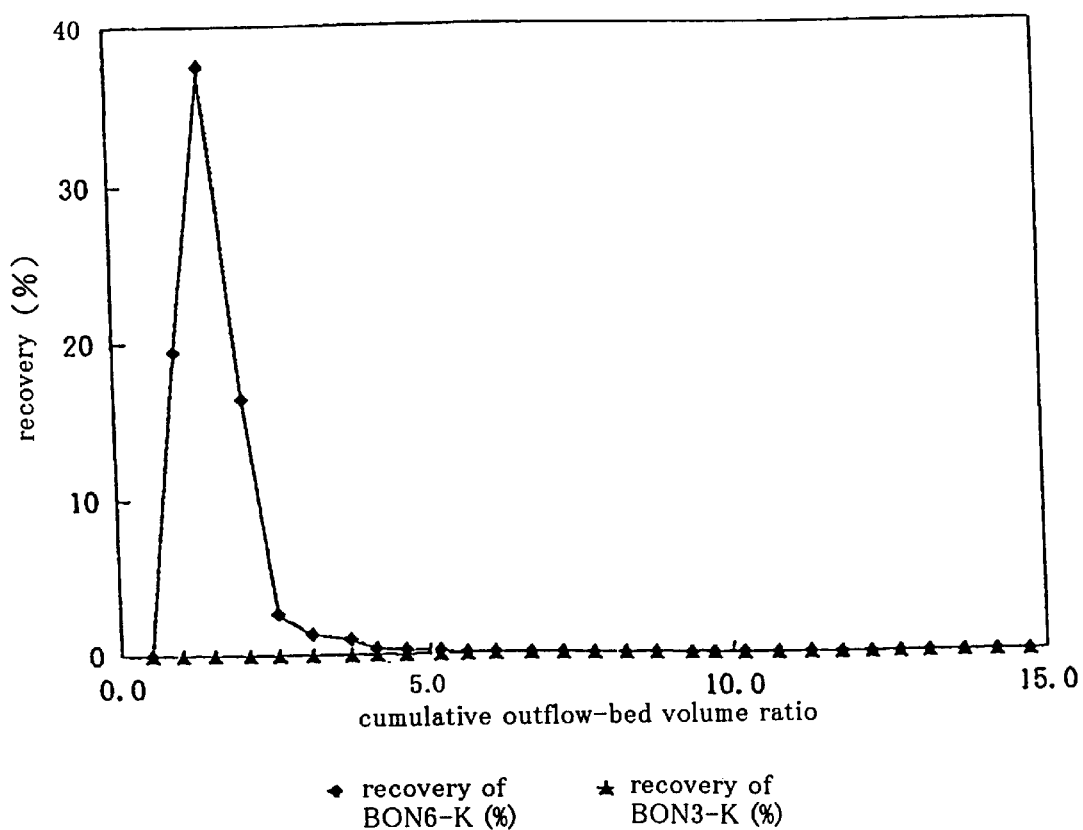
FIG. 1 is a chart showing the recoveries of BON6-K salt and BON3-K salt obtained by using water as a developer in Example 1.

The wording "treating with solvent" as used herein refers to, for example, those procedures in which alkali metal salts of hydroxynaphthalenecarboxylic acids which have been adsorbed in advance to an adsorbent are selectively extracted or eluted from the column packed with the adsorbent using a particular solvent.

The term "hydroxynaphthalenecarboxylic acids" as used herein include not only hydroxynaphthalenemonocarboxylic acids but also polycarboxylic acids such as dicarboxylic acids, tricarboxylic acids, tetracarboxylic acids, and so on.

Among the nonionic porous synthetic adsorbents used in the present invention, aromatic copolymers mainly composed of styrene and divinylbenzene, and methacrylic copolymers mainly composed of monomethacrylate and dimethacrylate are already known. Such nonionic porous synthetic adsorbents which comprise, as the basic structure, aromatic copolymers mainly composed of styrene and divinylbenzene include, for example, Diaion HP10, HP20, HP21, HP30, HP40, HP50, SP850, and SP205 (trade names: Mitsubishi Chemical Corp.), and Amberlite XAD2 and XAD4 (trade names: Rohm and Haas Co.). Examples of nonionic porous synthetic adsorbent which comprises, as the basic structure, methacrylic copolymer mainly composed of monomethacrylate and dimethacrylate are Diaion HP2MG, Amberlite XAD7 and XAD 8, and others.

The nonionic porous synthetic adsorbents used in the present invention are porous cross-linked polymers, and have specific surface areas and pore volumes in significant quantities. A suitable adsorbent has a specific surface area of 100 m$^2$/g or above, preferably 400 m$^2$/g or above, and a pore volume of 0.1 ml/g or above, preferably 0.5 ml/g or above, and more preferably 1.0 ml/g or above. A specific surface area less than 100 m$^2$/g or a pore volume less than 0.1 ml/g has a tendency to affect the adsorbing capacity, and thus, lower the separating ability of the adsorbent.

BON6 is produced by Kolbe-Schmitt process as described above, and in such process, BON3 is also produced as a by-product. The amount of BON3 thus generated varies depending on the process used for producing BON6. Since BON3 is a useful compound in itself, for example, as an intermediate for pigments, one of the objects of the present invention is to separate the alkali metal salt of BON6 and the alkali metal salt of BON3 from each other. According to the present invention, the alkali salt of BON6 can also be purified in a similar manner from other impurities or by-products.

In the present invention, various hydroxynaphthalenecarboxylic acids in which only the carboxyl groups are in the form of alkali metal salts can be separated and purified. Such products are usually generated from a mixture of alkali metal salts of hydroxynaphthalenecarboxylic acids prepared, for example, in Kolbe-Schmitt process, by converting only the alkali metal salts of the hydroxyl groups into the free form without neutralizing the mixture completely.

Such process is described below in detail with respect to reaction products including the potassium salt of BON3 (hereinafter referred to as BON3-K) and the potassium salt of BON6 (hereinafter referred to as BON6K). The reaction products containing excessive alkali are partially neutralized as necessary to leave potassium carboxylates, adsorbed to a nonionic porous synthetic adsorbent using the aqueous solution or in a mixed solvent of water and water-soluble organic solvent(s), and then treated with water or a mixed solvent of water and water-soluble organic solvent(s). When only water is used in such treatment, BON6-K is firstly eluted from the adsorbent, while BON3-K is eluted quite slowly or remains adsorbed. Increase in the proportion of the water-soluble organic solvent(s) in the developer facilitates the elution of BON3-K. Where the proportion of the water-soluble organic solvent is low, separation between BON3-K and BON6-K is definite, although the amount of eluted BON3-K is small. As the proportion of the water-soluble organic solvent(s) increases, the amount of eluted BON3-K also increases, but overlapping of the elution peaks for BON3-K and BON6-K becomes apparent.

Although this tendency varies depending on, for example, the types of adsorbent, water-soluble organic solvent(s), and alkali metal used as well as the degree of neutralization, conditions under which the intended compound(s) are most efficiently recovered can be experimentally determined. The dipotassium salt of BON3,6 is more weakly adsorbed by the above nonionic adsorbent than BON6-K, and separation of this salt may also be confirmed experimentally.

The treatment may be conducted by a batch method using water or water and water-soluble organic solvent(s) which dissolve alkali metal salts of hydroxynaphthalenecarboxylic acids, or may also be conducted continuously or in batch using column chromatography method. In a batch method, since the alkali metal salt of BON3 is eluted quite slowly or remains adsorbed in contrast to the alkali metal salt of BON6 as described above, an aqueous solution containing the reaction products may be applied to the adsorbent, and recovered as an aqueous solution containing the alkali metal salt of BON6 by allowing only the alkali metal salt of BON3 to be adsorbed to the adsorbent. If it is desired to recover the alkali metal salt of BON3, it may be extracted from the components remaining adsorbed to the adsorbent using water-soluble organic solvent(s) or a mixed solvent thereof with water. In column chromatography method, the mixture may be firstly developed using only water, and then progressively developed using a developer comprising water and water-soluble organic solvent(s) mixed at an appropriate ratio. Alternatively, a developer comprising water and water-soluble organic solvent(s) mixed at a ratio which separately elutes the two products may also be used from the beginning. The development may also be conducted progressively by altering the ratio between water and water-soluble organic solvent(s) in the developer gradually.

Examples of a water-soluble organic solvent which may be used in the present invention are alcohols such as methanol, ethanol, n-propyl alcohol, isopropyl alcohol, and tert-butanol, ethers such as dioxane and tetrahydrofuran, ketones such as acetone, amides such as dimethylformamide, sulfur-containing compounds such as dimethylsulfoxide. Two or more of such organic solvents may be mixed for use. In addition, solvents less soluble in water, for example, alcohols such as n-butanol, esters such as methyl formate and methyl acetate, and ketones such as methyl ethyl ketone may also be used to the extent that it does not separate during development. Particularly preferred water-soluble organic solvents are alcohols, in particular, methanol, ethanol, propyl alcohol, and the like. Furthermore, different kinds of solvent may also be used sequentially for development.

Although the alkali metals which form salts of hydroxynaphthalenecarboxylic acids may include sodium, potassium, lithium and the like, sodium and potassium are preferred for industrial purpose. The reaction products obtained in Kolbe-Schmitt process are usually in the form of salts with regard to both of the hydroxyl groups and the carboxyl groups. Therefore, when such reaction products are to be used as a raw material, the amount of acid which is required to leave only the salts in the form of carboxylates may be determined, and a corresponding amount of an acid may be used to neutralize the raw material. The acid used for this purpose may be a strong acid such as hydrochloric acid or sulfuric acid, an organic acid such as acetic acid or propionic acid, or an acidic gas such as carbon dioxide or hydrogen sulfide.

The proportion of an alkali metal salt of a particular hydroxynaphthalenecarboxylic acid may also be increased by repeating the treatment according to the process of the present invention. Furthermore, the proportion and concentration of an alkali metal salt of a particular hydroxynaphthalenecarboxylic acid may also be increased using, for example, a similar moving-bed process such as those described in Japanese Patent Publication No. H249159, A (1990).

The present invention is further described by making reference to Examples below.

EXAMPLE 1

In order to prepare a column for separation and purification, a glass column having an internal diameter of 28 mm and a height of 400 mm was packed with 200 ml of a nonionic porous synthetic adsorbent (Diaion HP20: Mitsubishi Chemical Corp., specific surface area: 605 m$^2$/g, pore volume (mercury press-in method): 1.18 ml/g), which comprises as the basic structure an aromatic copolymer mainly composed of styrene and divinylbenzene, suspended in a developer (water or water-methanol mixture, methanol concentration: 0–90% by weight).

Separately, 9.0 g of 2-hydroxynaphthalene-6-carboxylic acid potassium salt (hereinafter referred to as BON6K) and 1.0 g of 2-hydroxynaphthalene-3-carboxylic acid potassium salt (hereinafter referred to as BON3-K) were dissolved in the developer to prepare 100 g of a stock solution (when the developer contained 0% by weight methanol (ion-exchanged water), 8.1 g of BON6-K and 0.9 g of BON3-K were used).

Next, 6.2 ml of the stock solution (the weight of 6.2 ml of the stock solution being separately measured) was precisely measured out, injected into the top of the synthetic adsorbent bed in the above-described column, and then developed at room temperature using the developer at 6.2 ml/min. The developer outflowing from the bottom of the column was then collected in about 15–100 ml fractions. (The relations between methanol concentrations and fraction volumes are shown in Table 1).

Each fraction thus collected was weighed, and determined its concentrations for BON6 and BON3 with high performance liquid chromatography devices (model 600 E pump and model 486 UV detector: Waters Corp.). The weights of the potassium salts in the fraction were then calculated using the concentrations thus determined.

The results of such analysis are graphically depicted in FIGS. 1, 3, 5, 7, 9, and 11 in which the abscissa provides the volume of eluted developer expressed as its ratio to the volume of packed adsorbent (cumulative outflow-bed volume ratio) and the ordinate provides the recoveries of BON6-K and BON3-K in each fraction calculated according to the following equations. In addition, the results are also depicted graphically in FIGS. 2, 4, 6, 8, 10, and 12 in which the abscissa provides the cumulative outflow-bed volume ratio and the ordinate provides the proportions of BON6-K and BON3-K calculated according to the following equations. (The relations between methanol concentrations and Figures are shown in Table 1).

Recovery of BON6-K (%)=100×(the weight of BON6-K in the fraction)/(the weight of BON6-K in the raw material)

Recovery of BON3-K (%)=100×(the weight of BON3-K in the fraction)/(the weight of BON3-K in the raw material)

Proportion of BON6-K (%)=100×(the weight of BON6-K in the fraction)/(the total weight of BON6-K and BON3-K in the fraction)

Proportion of BON3-K (%)=100×(the weight of BON3-K in the fraction)/(the total weight of BON6-K and BON3-K in the fraction)

TABLE 1

Figure 2:
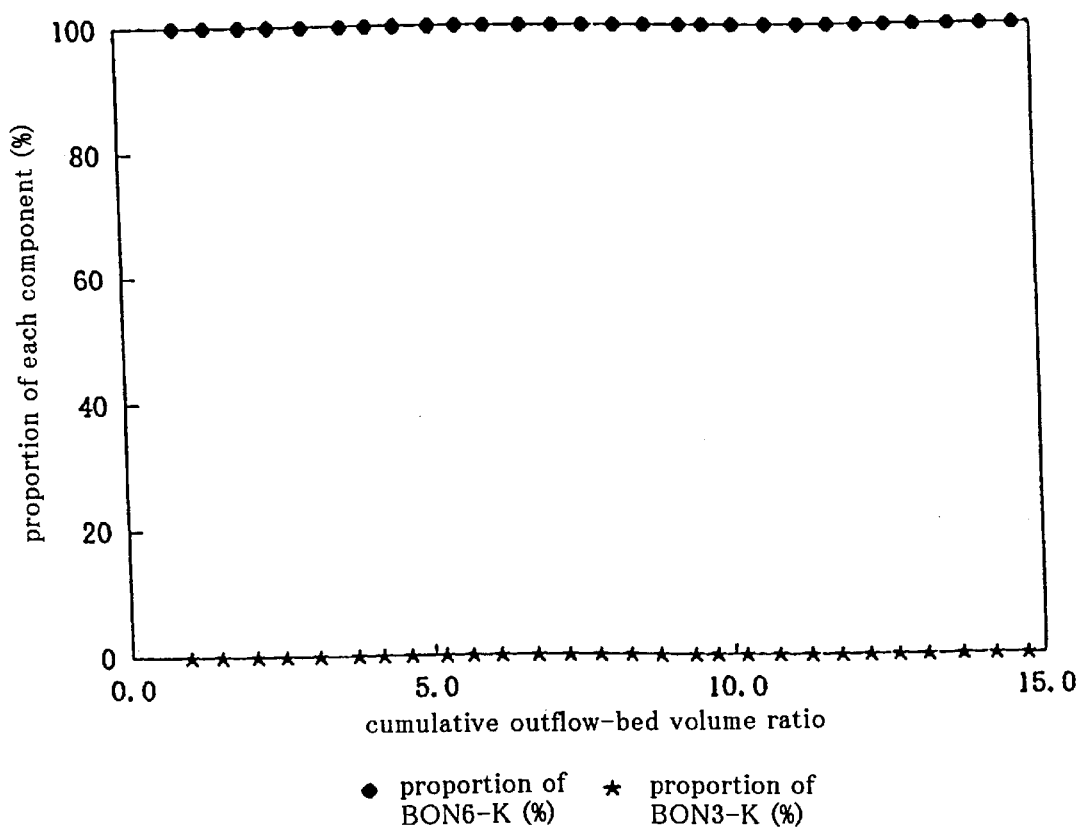
FIG. 2 is a chart showing the proportions of components, BON6-K salt and BON3-K salt, obtained by using water as a developer in Example 1.
Figure 3:
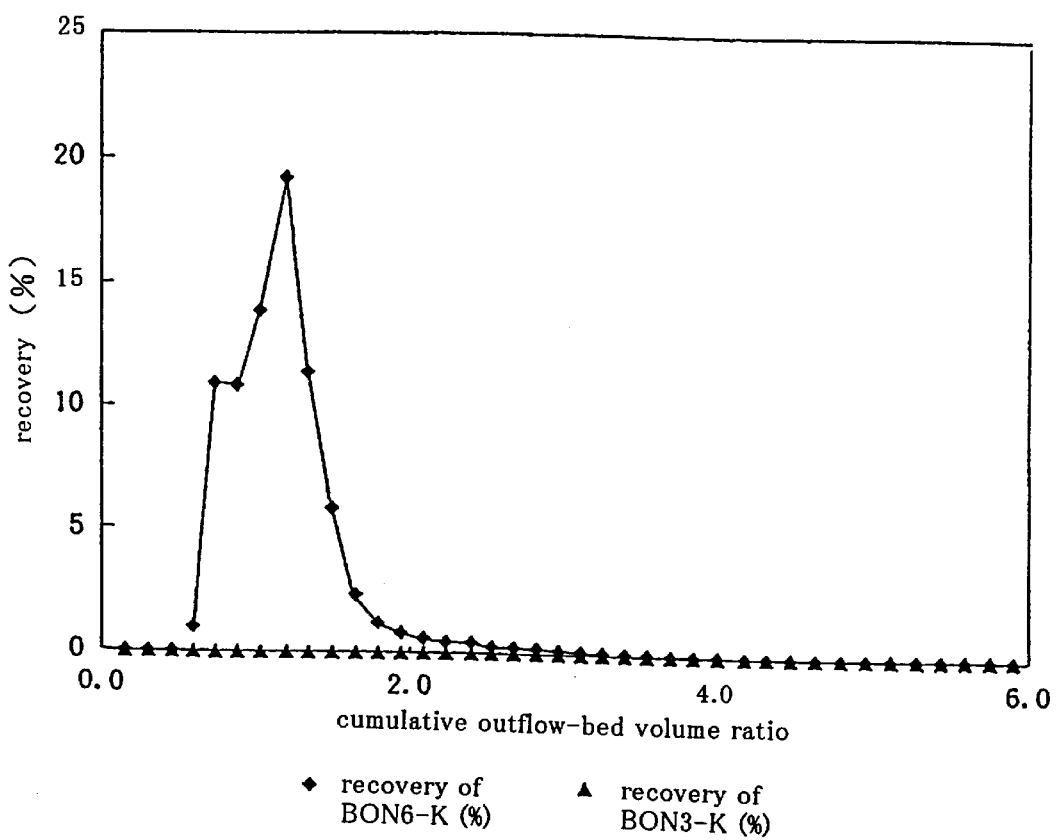
FIG. 3 is a chart showing the recoveries of BON6-K salt and BON3-K salt obtained by using 90% by weight water and 10% by weight methanol as a developer in Example 1.
Figure 4:
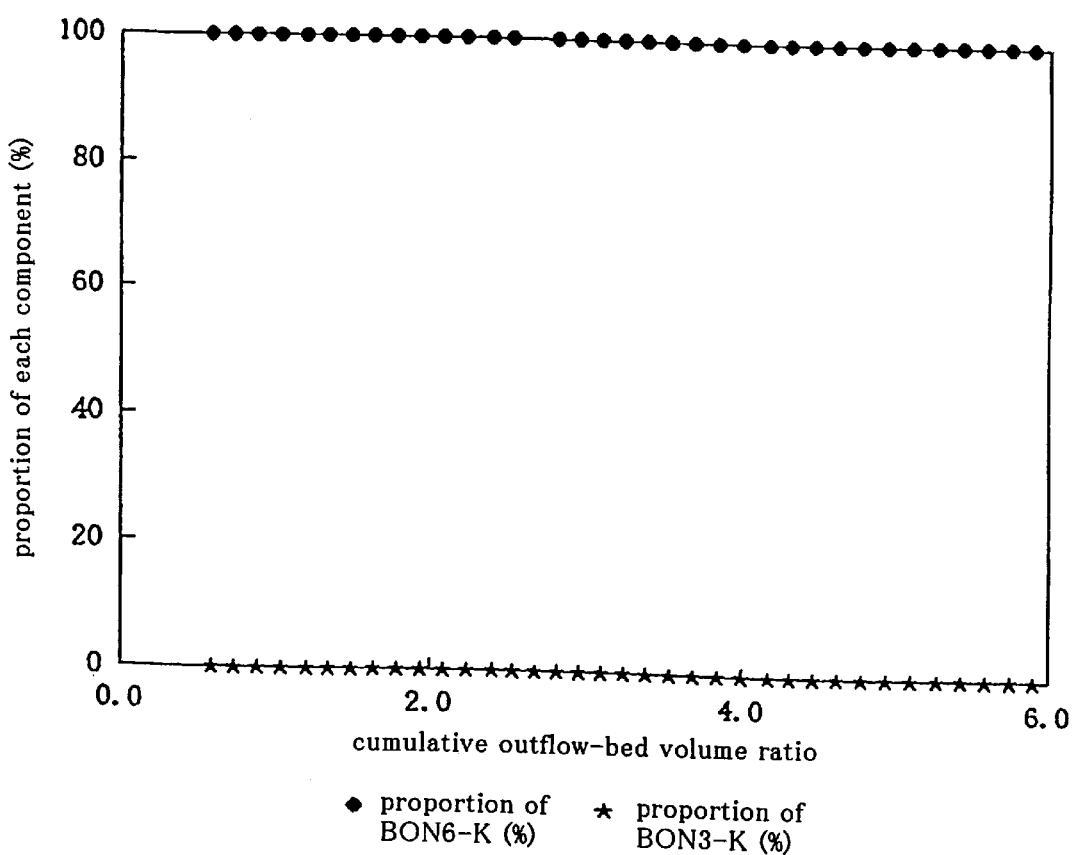
FIG. 4 is a chart showing the proportions of components, BON6-K salt and BON3-K salt, obtained by using 90% by weight water and 10% by weight methanol as a developer in Example 1.
Figure 5:
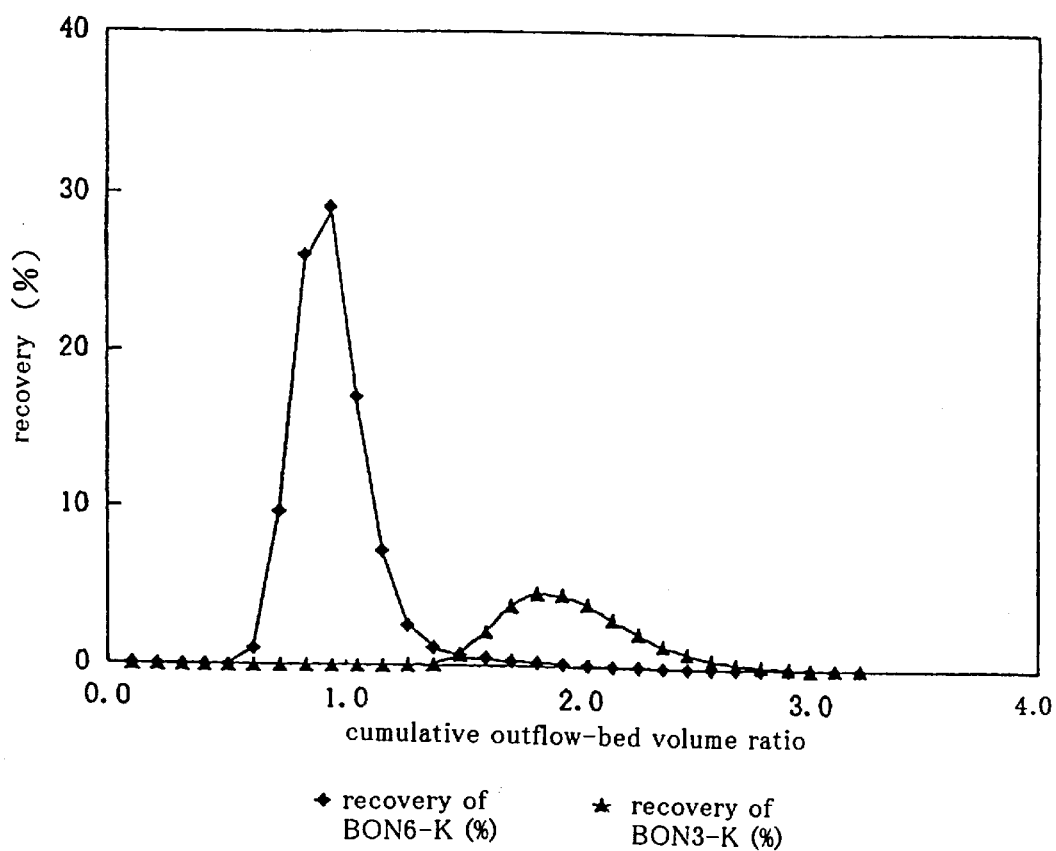
FIG. 5 is a chart showing the recoveries of BON6-K salt and BON3-K salt obtained by using 70% by weight water and 30% by weight methanol as a developer in Example 1.
Figure 6:
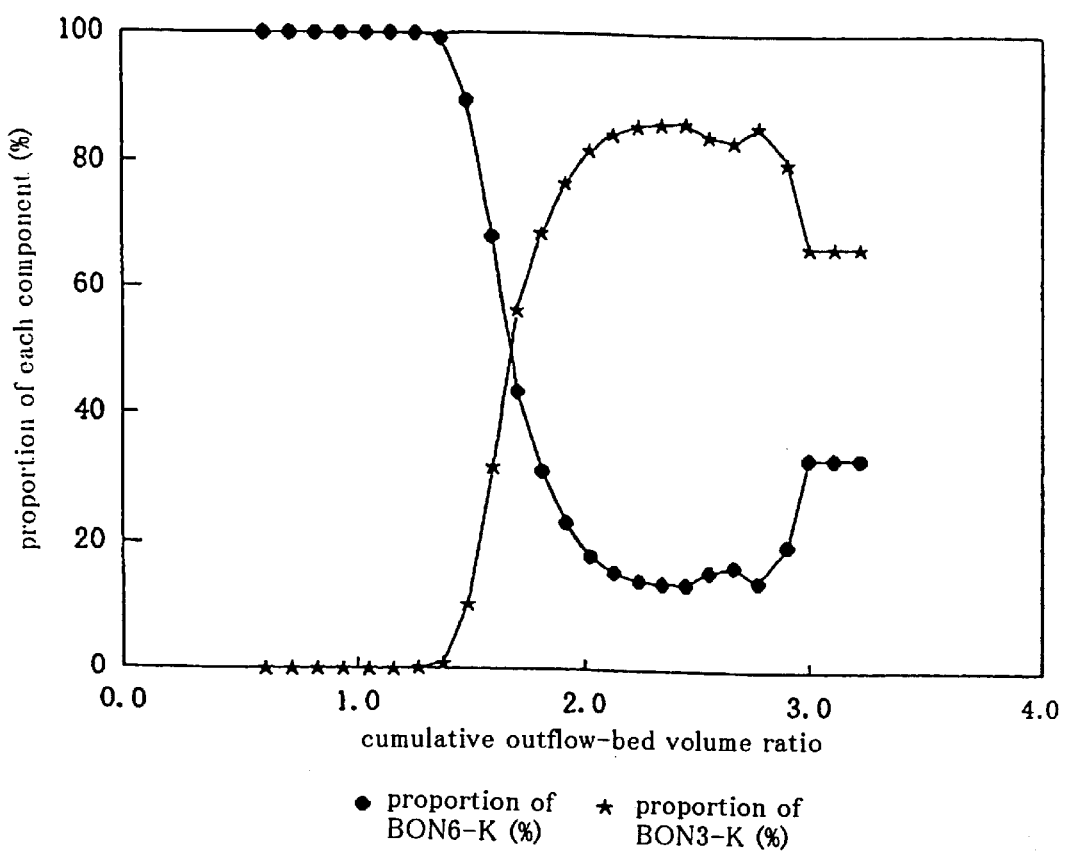
FIG. 6 is a chart showing the proportions of components, BON6-K salt and BON3-K salt, obtained by using 70% by weight water and 30% by weight methanol as a developer in Example 1.
Figure 7:
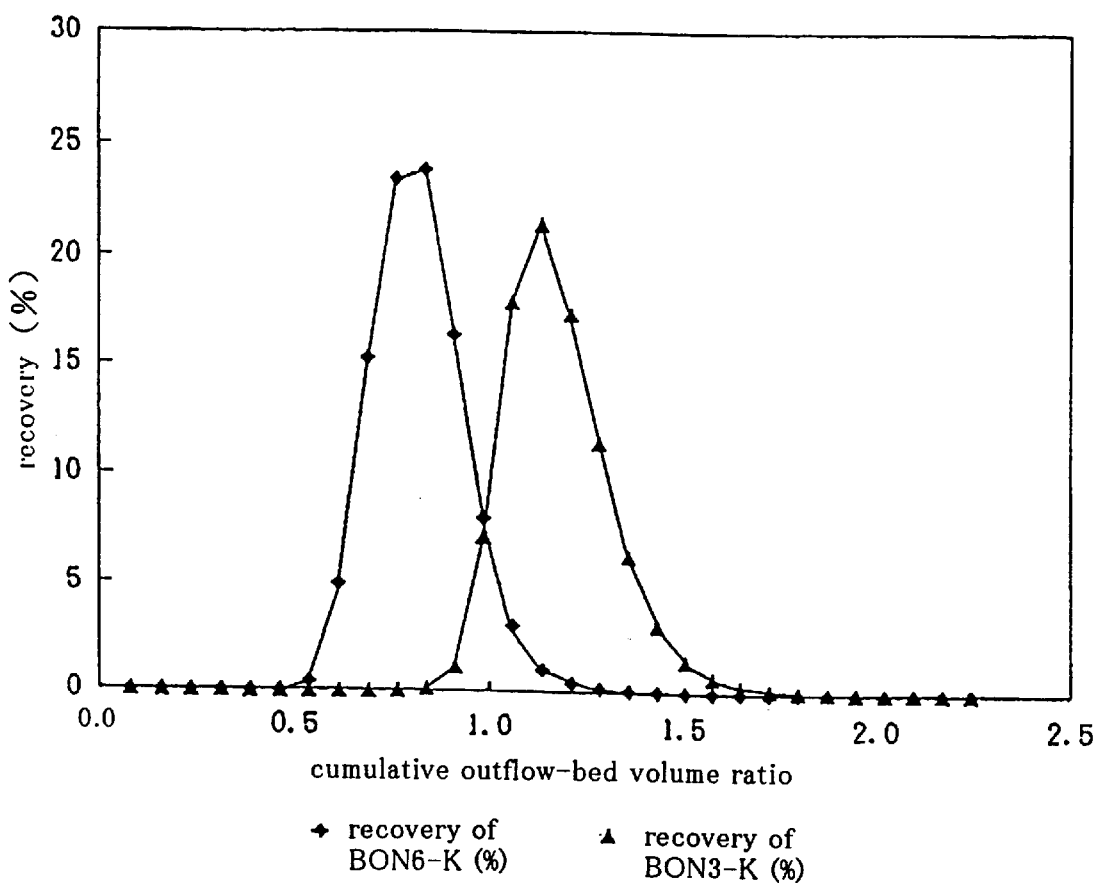
FIG. 7 is a chart showing the recoveries of BON6-K salt and BON3-K salt obtained by using 50% by weight water and 50% by weight methanol as a developer in Example 1.
Figure 8:
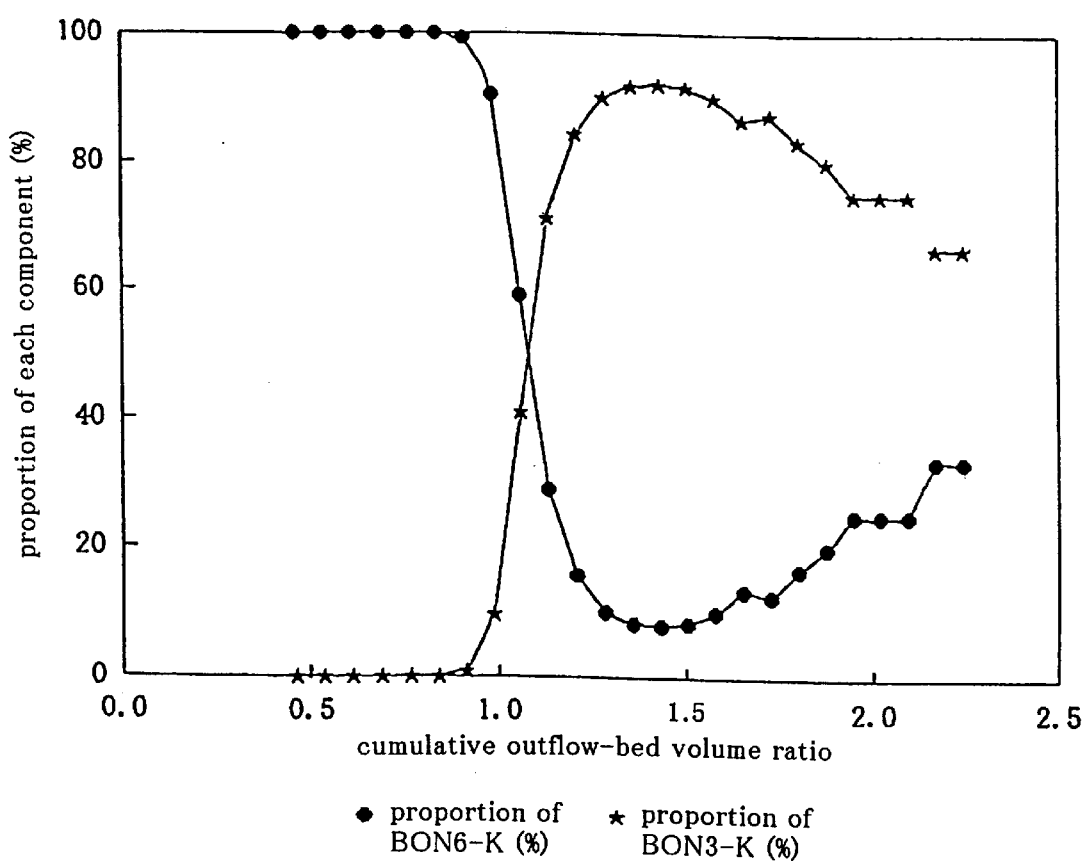
FIG. 8 is a chart showing the proportions of components, BON6-K salt and BON3-K salt, obtained by using 50% by weight water and 50% by weight methanol as a developer in Example 1.
Figure 9:
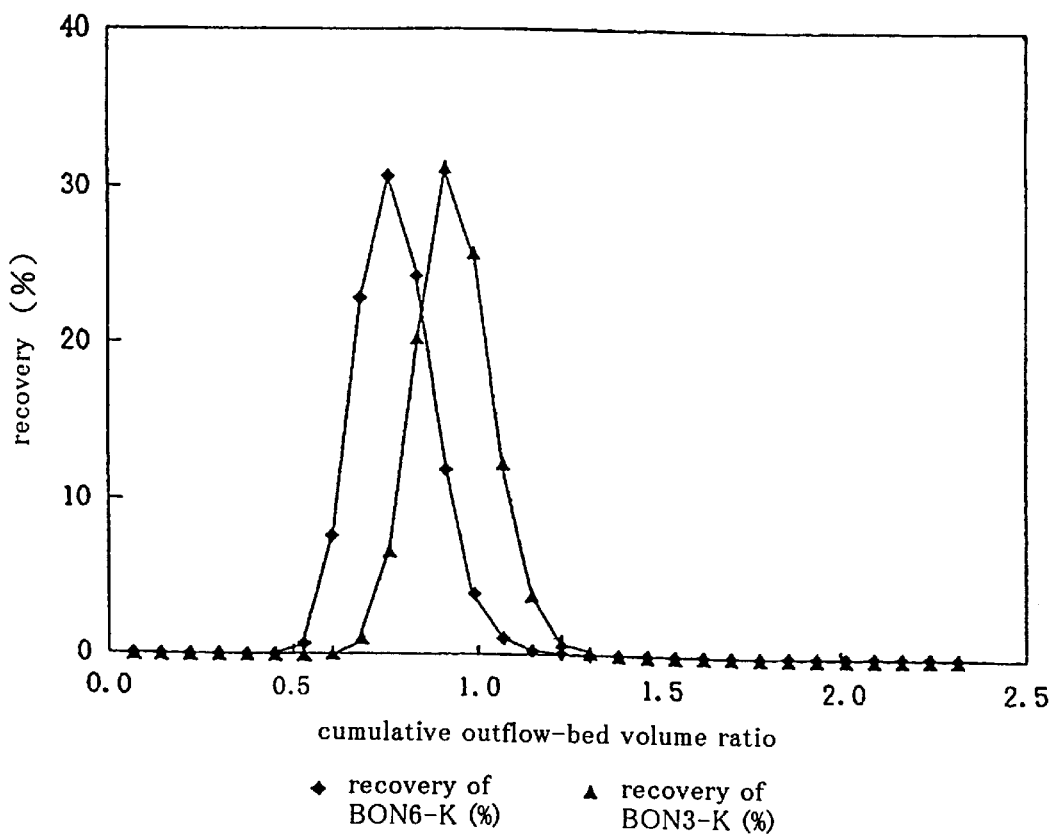
FIG. 9 is a chart showing the recoveries of BON6-K salt and BON3-K salt obtained by using 30% by weight water and 70% by weight methanol as a developer in Example 1.
Figure 10:
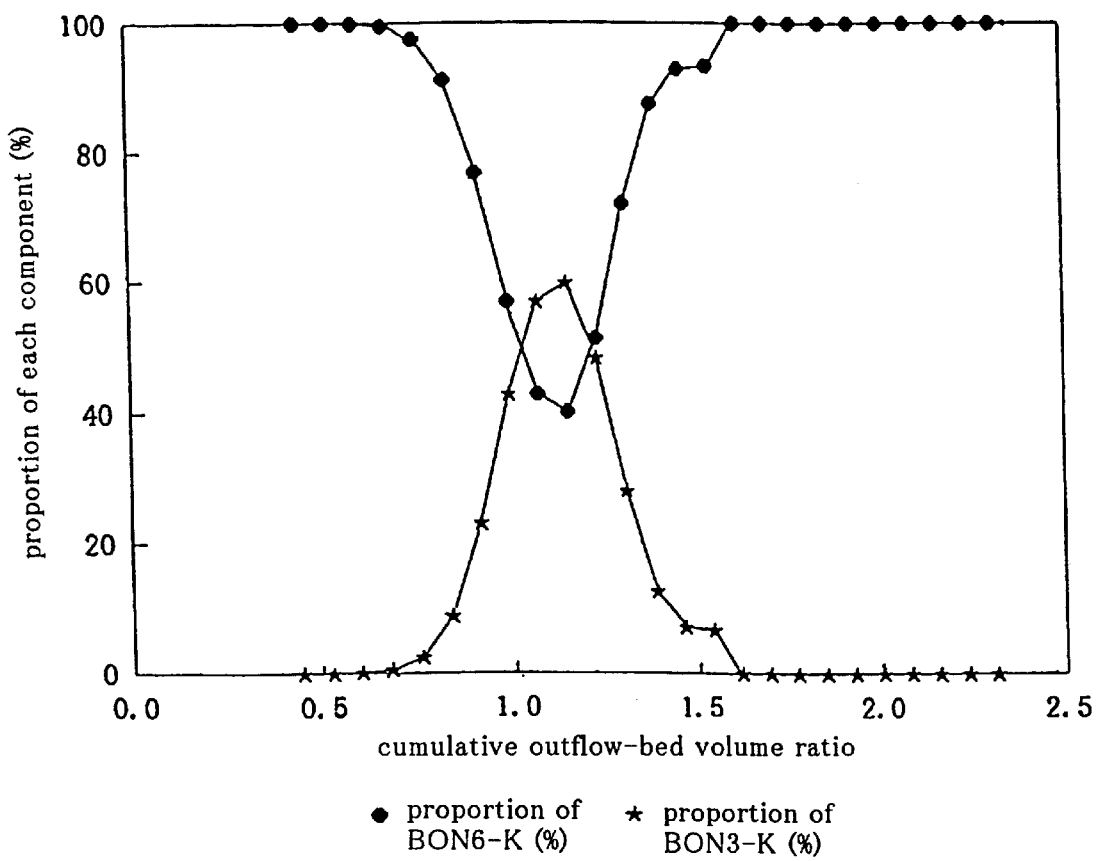
FIG. 10 is a chart showing the proportions of components, BON6-K salt and BON3-K salt, obtained by using 30% by weight water and 70% by weight methanol as a developer in Example 1.
Figure 11:
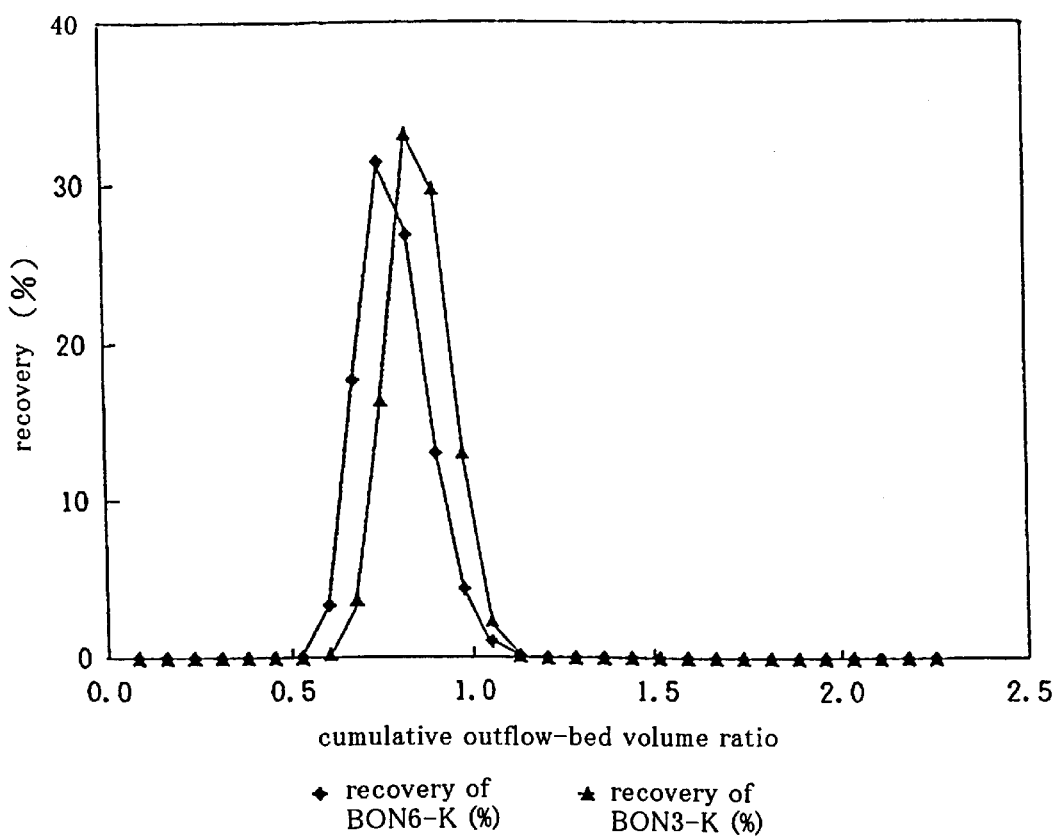
FIG. 11 is a chart showing the recoveries of BON6-K salt and BON3-K salt obtained by using 10% by weight water and 90% by weight methanol as a developer in Example 1.
Figure 12:
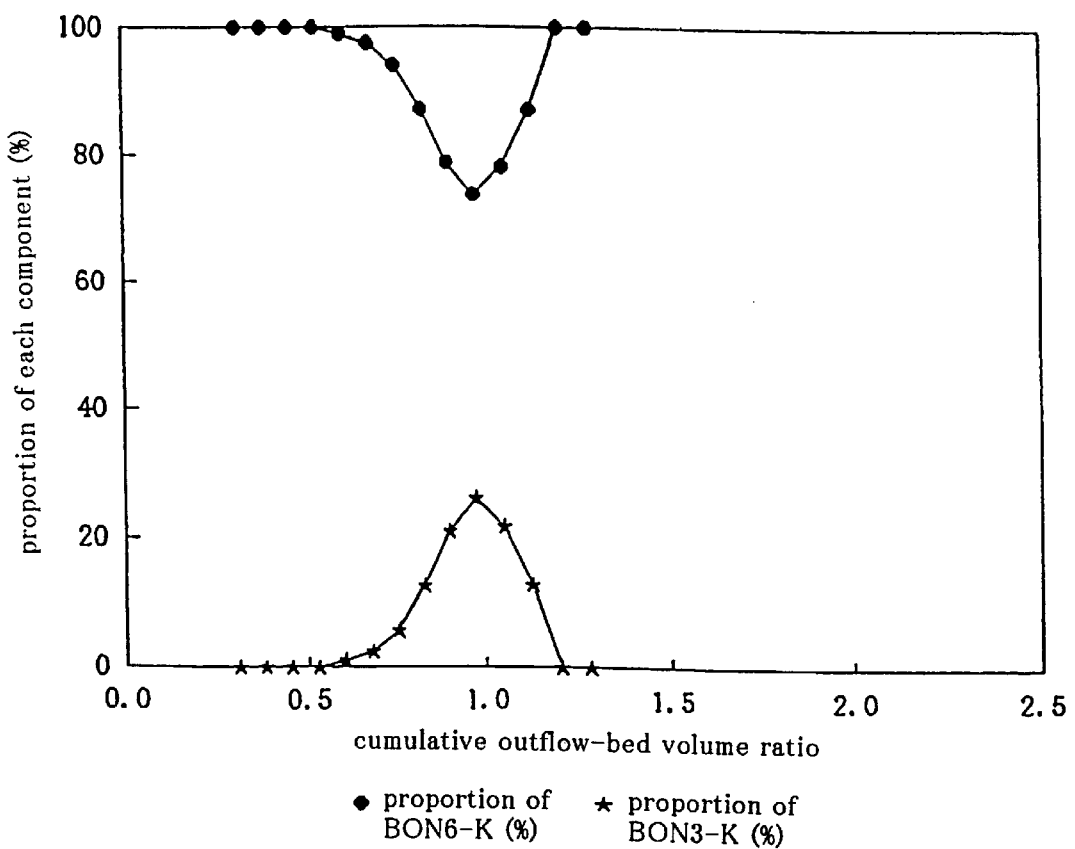
FIG. 12 is a chart showing the proportions of components, BON6-K salt and BON3-K salt, obtained by using 10% by weight water and 90% by weight methanol as a developer in Example 1.

| Methanol concentration | Fraction volume | Correlation chart between cumulative outflow-bed volume ratio and recoveries | Correlation chart between cumulative outflow-bed volume ratio and proportions |
|---|---|---|---|
| 0% | 100 ml | FIG. 1 | FIG. 2 |
| 10% | 30 ml | FIG. 3 | FIG. 4 |
| 30% | 20 ml | FIG. 5 | FIG. 6 |
| 50% | 15 ml | FIG. 7 | FIG. 8 |
| 70% | 15 ml | FIG. 9 | FIG. 10 |
| 90% | 15 ml | FIG. 11 | FIG. 12 |

The results of separation and purification of BON6-K and BON3-K are summarized in Table 2 on the basis of FIGS. 1–12.

TABLE 2

| Methanol concentration | Purification of BON6-K | | Purification of BON3-K | |
|---|---|---|---|---|
| | proportion (%) | recovery (%) | proportion (%) | recovery (%) |
| 0% | 100 | 80.4 | — | — |
| 10% | 100 | 80.4 | — | — |
| 30% | >99 | 94.1 | >80 | 13.2 |
| 50% | >99 | 84.4 | >80 | 41.1 |
| 70% | >99 | 31.2 | >50 | 16.3 |
| 90% | >99 | 3.5 | >20 | 45.3 |

EXAMPLE 2

The development was conducted as in Example 1 using 0% by weight methanol (ion-exchanged water), with the exceptions that BON6-Na was used in place of BON6-K and BON3-Na was used in place of BON3-K and that the solution outflowing from the bottom of the column was collected in about 100 ml fractions.

Figure 13:
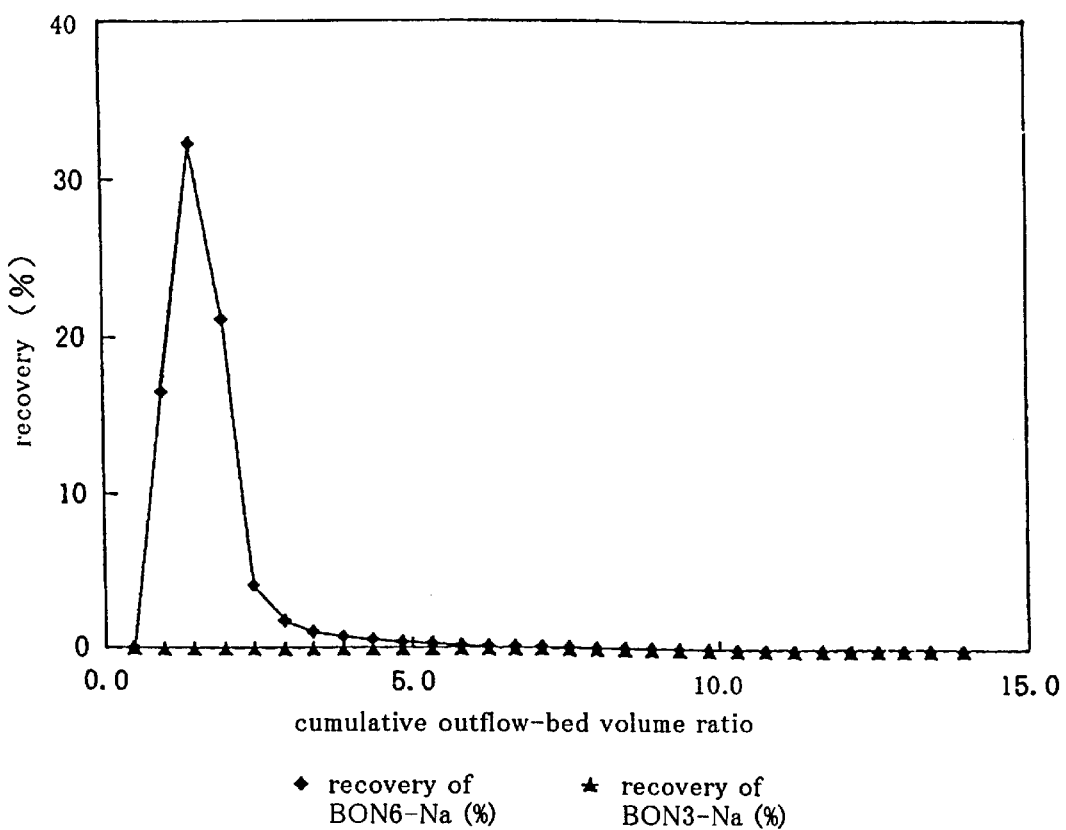
FIG. 13 is a chart showing the recoveries of BON6-Na salt and BON3-Na salt obtained by using only water as a developer in Example 2.
Figure 14:
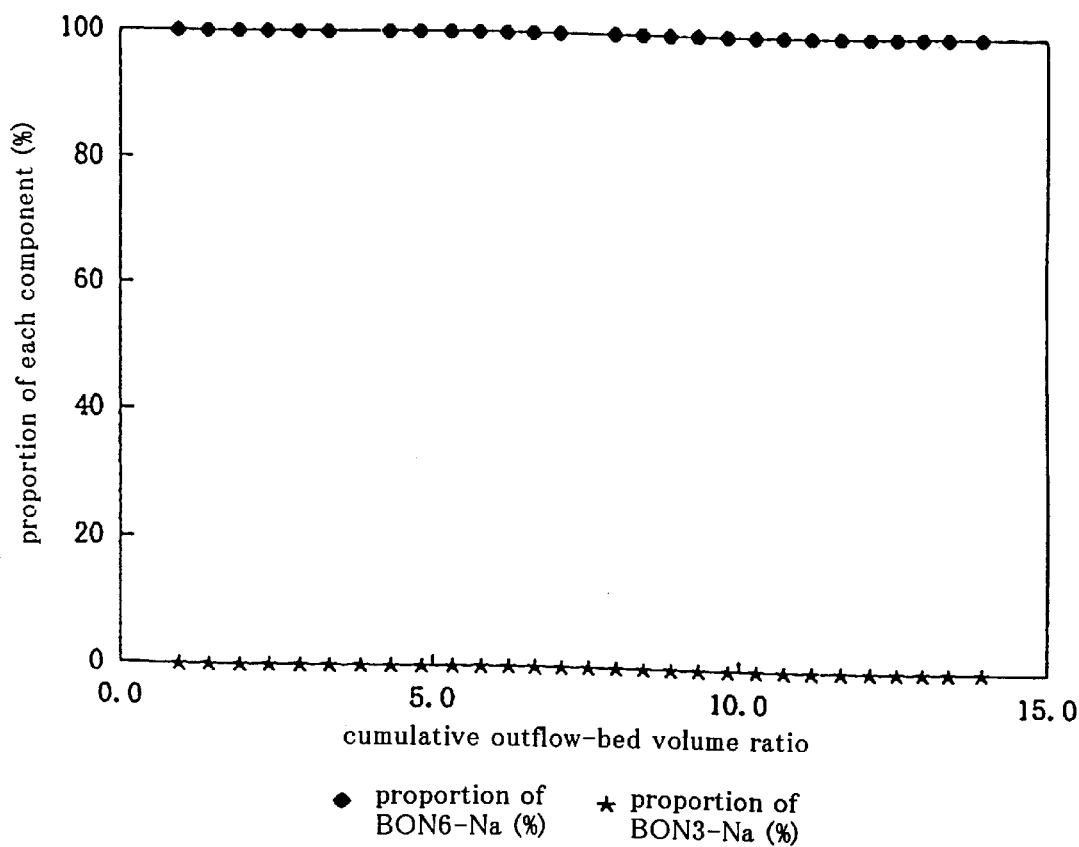
FIG. 14 is a chart showing the proportions of components, BON6-Na salt and BON3-Na salt, obtained by using only water as a developer in Example 2.

Each faction thus collected were then weighed, and measured for its BON6 and BON3 concentrations to calculate the weights of the sodium salts in the fraction, as in Example 1. The recoveries of BON6-Na and BON3-Na in each fraction are each shown in FIG. 13, and the proportions of BON6-Na and BON3-Na are each shown in FIG. 14.

BON3-Na was not eluted, and BON6-Na could be recovered at the proportion of 100% and at the recovery of 80.1%.

EXAMPLE 3

The development was conducted as in Example 1 with the exceptions that Diaion SP850 (specific surface area: 995 m$^2$/g, pore volume (nitrogen absorption method): 1.20 ml/g; Mitsubishi Chemical Corp.) was used as an adsorbent, that the methanol concentration of 50% or 70% by weight was used for the developer, and that the solution outflowing from the bottom of the column was collected in about 20 ml fractions.

Each fraction thus collected was then weighed, and measured for its BON6 and BON3 concentrations to calculate the weights of the potassium salts in the fraction, as in Example 1. The recoveries of BON6-K and BON3-K in each fraction are shown in each of FIGS. 15 and 17, and the proportions of BON6-K and BON3-K are shown in each of FIGS. 16 and 18. (The relations between methanol concentrations and Figures are shown in Table 3.)

TABLE 3

Figure 15:
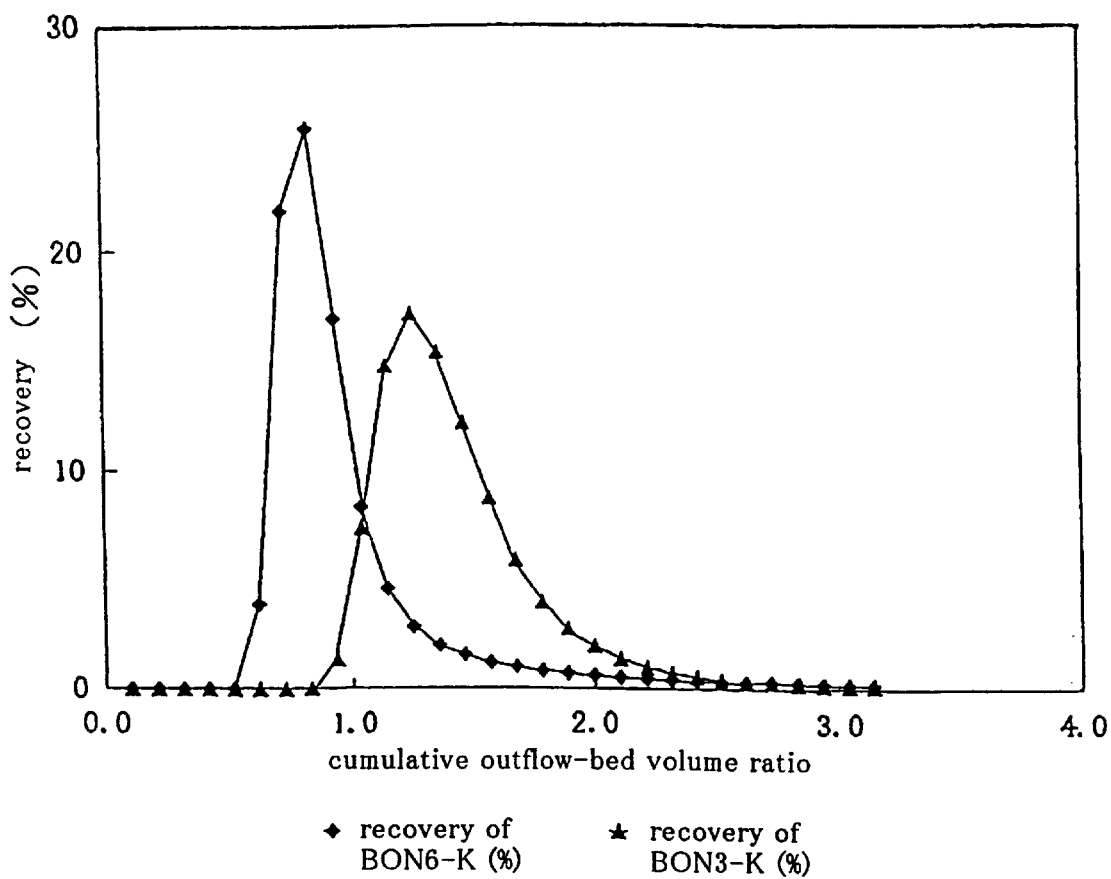
FIG. 15 is a chart showing the recoveries of BON6-K salt and BON3-K salt obtained by using 50% by weight water and 50% by weight methanol as a developer in Example 3.
Figure 16:
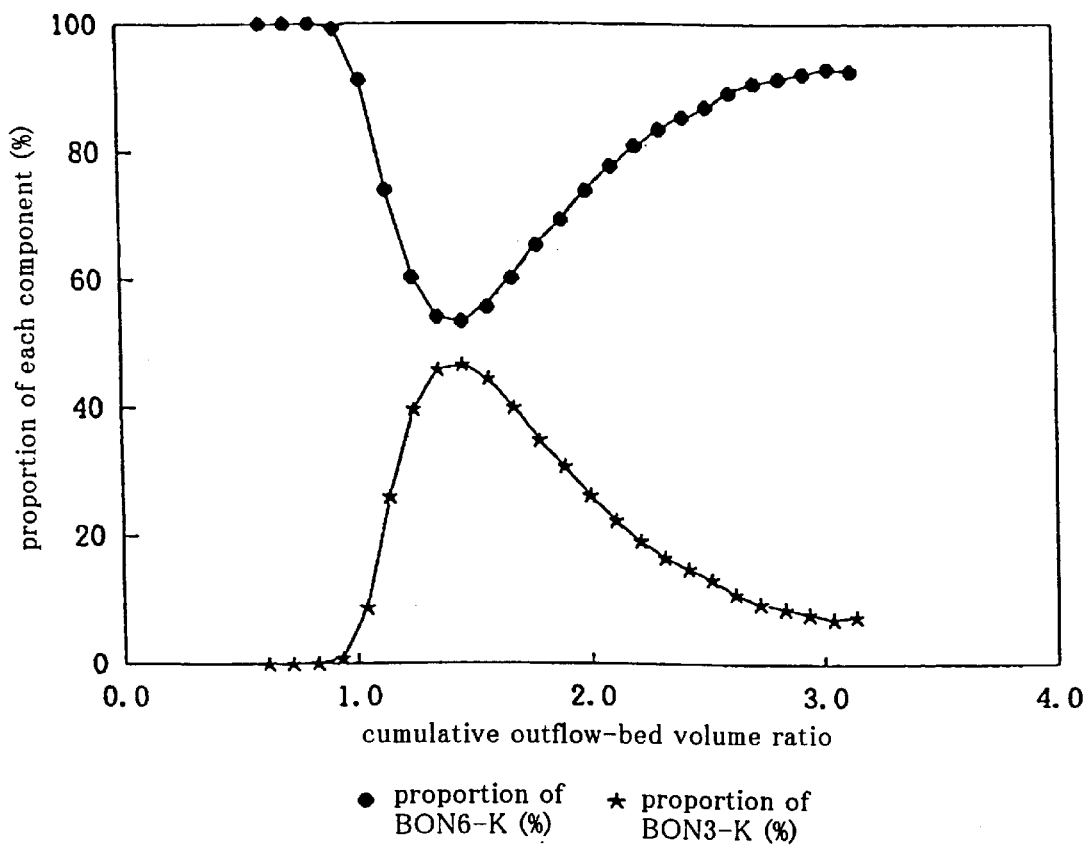
FIG. 16 is a chart showing the proportions of components, BON6-K salt and BON3-K salt, obtained by using 50% by weight water and 50% by weight methanol as a developer in Example 3.
Figure 17:
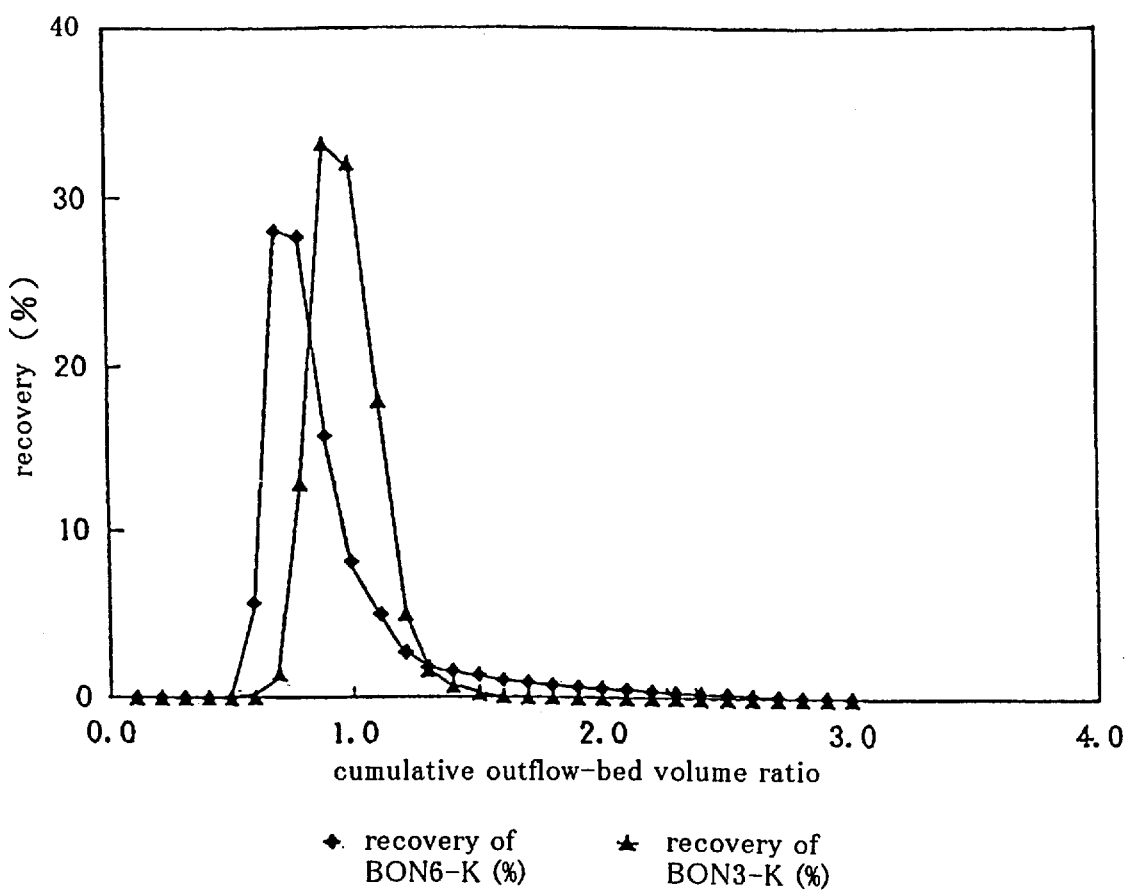
FIG. 17 is a chart showing the recoveries of BON6-K salt and BON3-K salt obtained by using 30% by weight water and 70% by weight methanol as a developer in Example 3.
Figure 18:
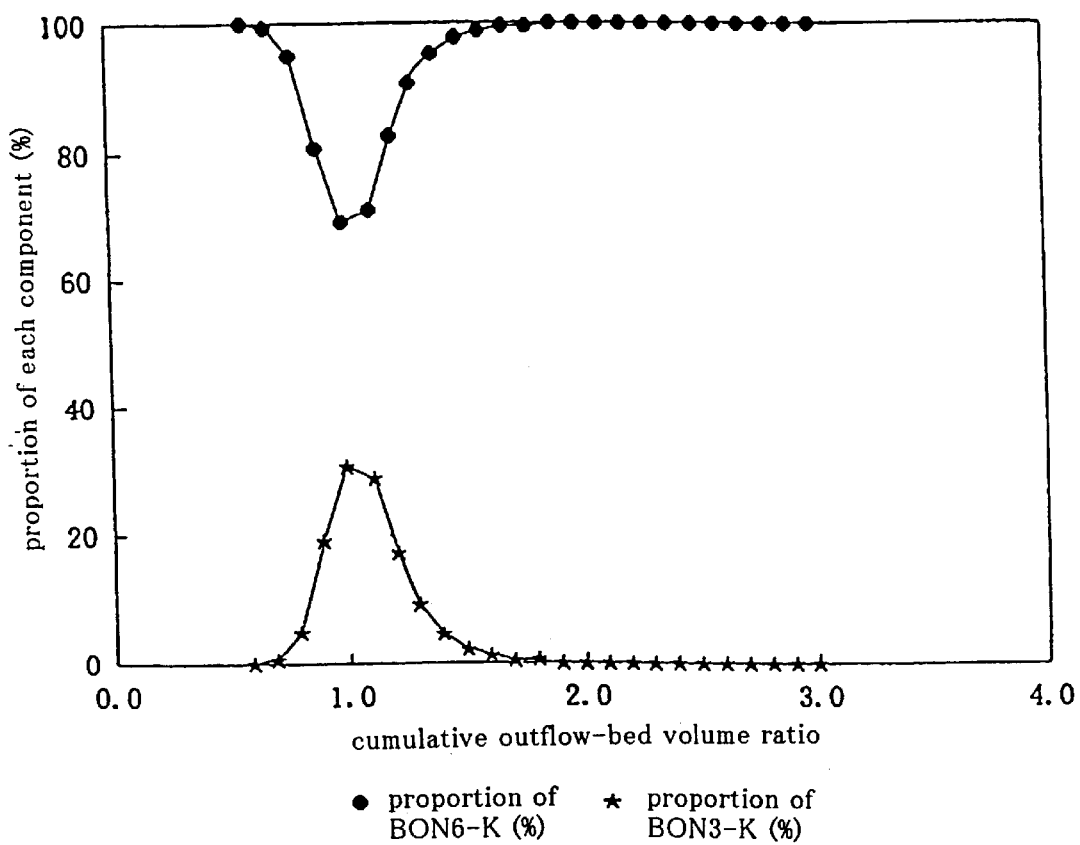
FIG. 18 is a chart showing the proportions of components, BON6-K salt and BON3-K salt, obtained by using 30% by weight water and 70% by weight methanol as a developer in Example 3.

| Methanol concentration | Correlation chart between cumulative outflow-bed volume ratio and recoveries | Correlation chart between cumulative outflow-bed volume ratio and proportions |
|---|---|---|
| 50% | FIG. 15 | FIG. 16 |
| 70% | FIG. 17 | FIG. 18 |

The results of separation and purification of BON6-K and BON3-K are summarized in Table 4 on the basis of FIGS. 15–18.

TABLE 4

| Methanol concentration | Purification of BON6-K | | Purification of BON3-K | |
|---|---|---|---|---|
| | proportion (%) | recovery (%) | proportion (%) | recovery (%) |
| 50% | >99 | 68.1 | >40 | 36.5 |
| 70% | >99 | 34.5 | >30 | 32.1 |

EXAMPLE 4

The development was conducted as in Example 1 with the exceptions that Diaion SP825 (specific surface area: 977 $m^2/g$, pore volume (nitrogen absorption method): 1.39 ml/g; Mitsubishi Chemical Corp.) was used as an adsorbent, that the methanol concentration of 0% or 50% by weight was used for the developer, and that the solution outflowing from the bottom of the column was collected in about 20 ml (50% by weight methanol) or about 100 ml (0% by weight methanol) fractions.

Each fraction thus collected was then weighed, and measured for its BON6 and BON3 concentrations to calculate the weights of the potassium salts in the fraction, as in Example 1. The recoveries of BON6-K and BON3-K in each fraction are shown in each of FIGS. 19 and 21, and the proportions of BON6-K and BON3-K are shown in each of FIGS. 20 and 22. (The relations between methanol concentrations and Figures are shown in Table 5.)

TABLE 5

Figure 19:
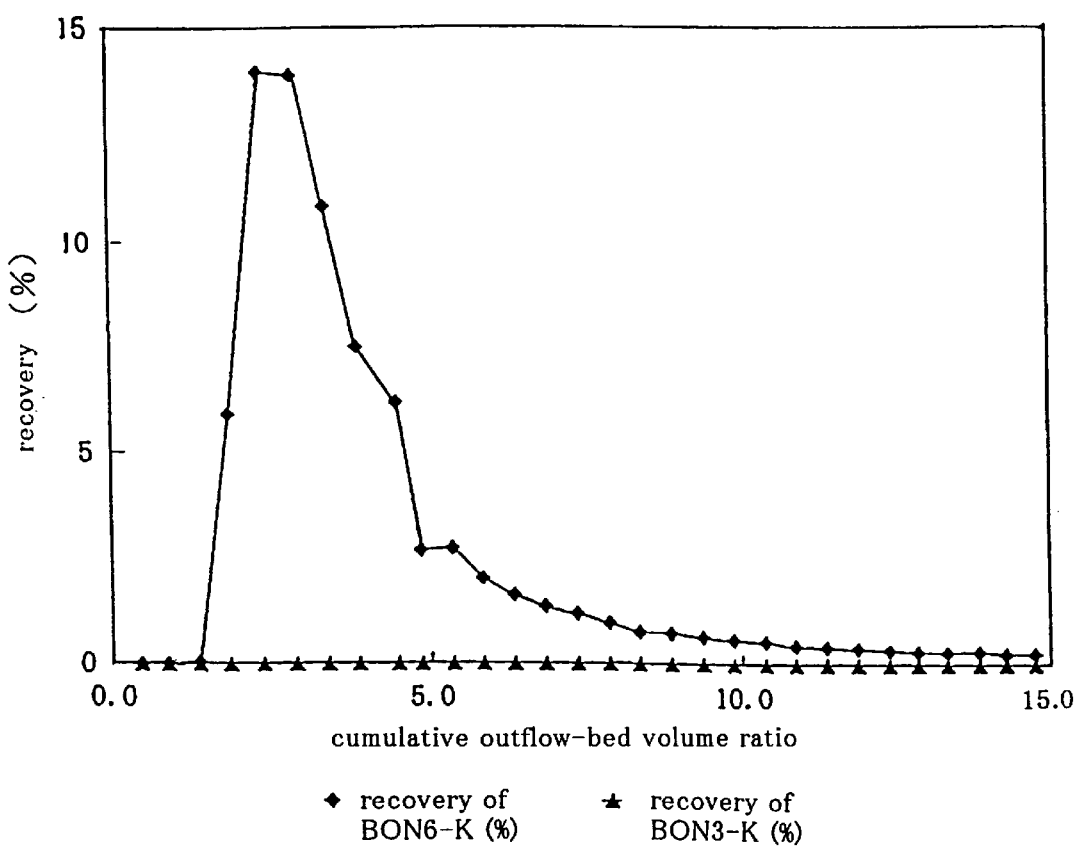
FIG. 19 is a chart showing the recoveries of BON6-K salt and BON3-K salt obtained by using water as a developer in Example 4.
Figure 20:
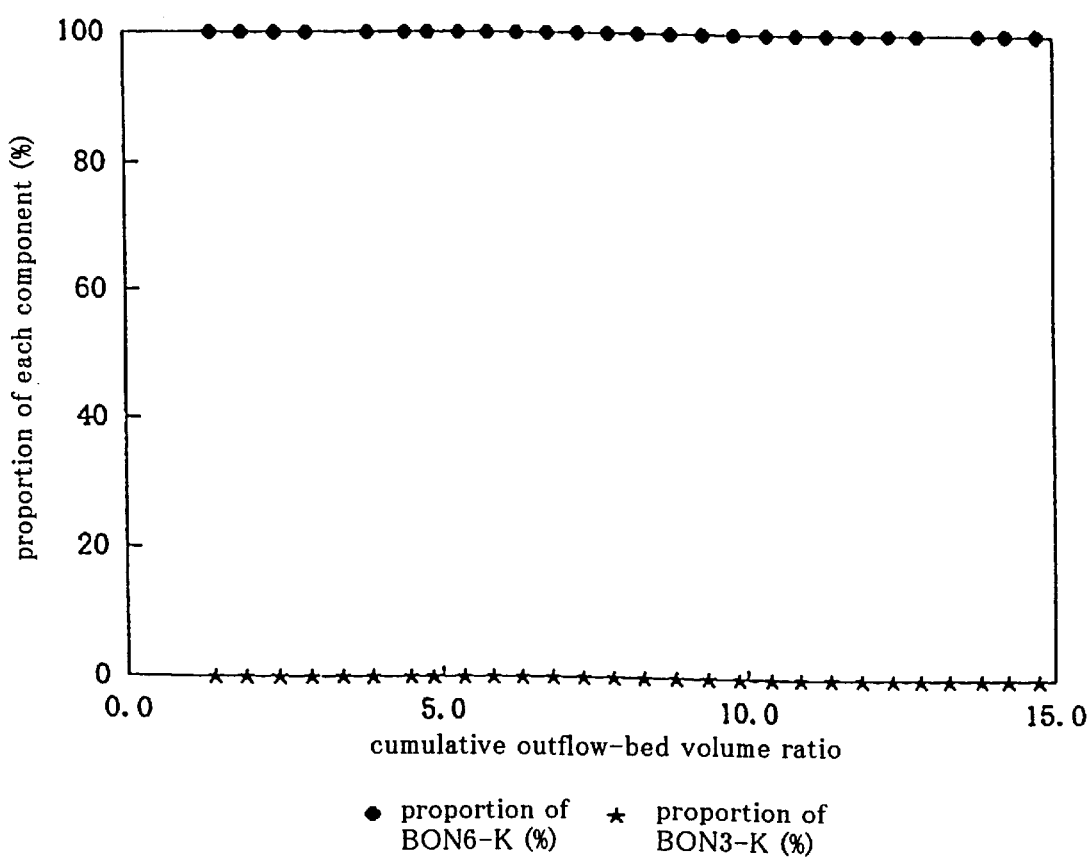
FIG. 20 is a chart showing the proportions of components, BON6-K salt and BON3-K salt, obtained by using water as a developer in Example 4.
Figure 21:
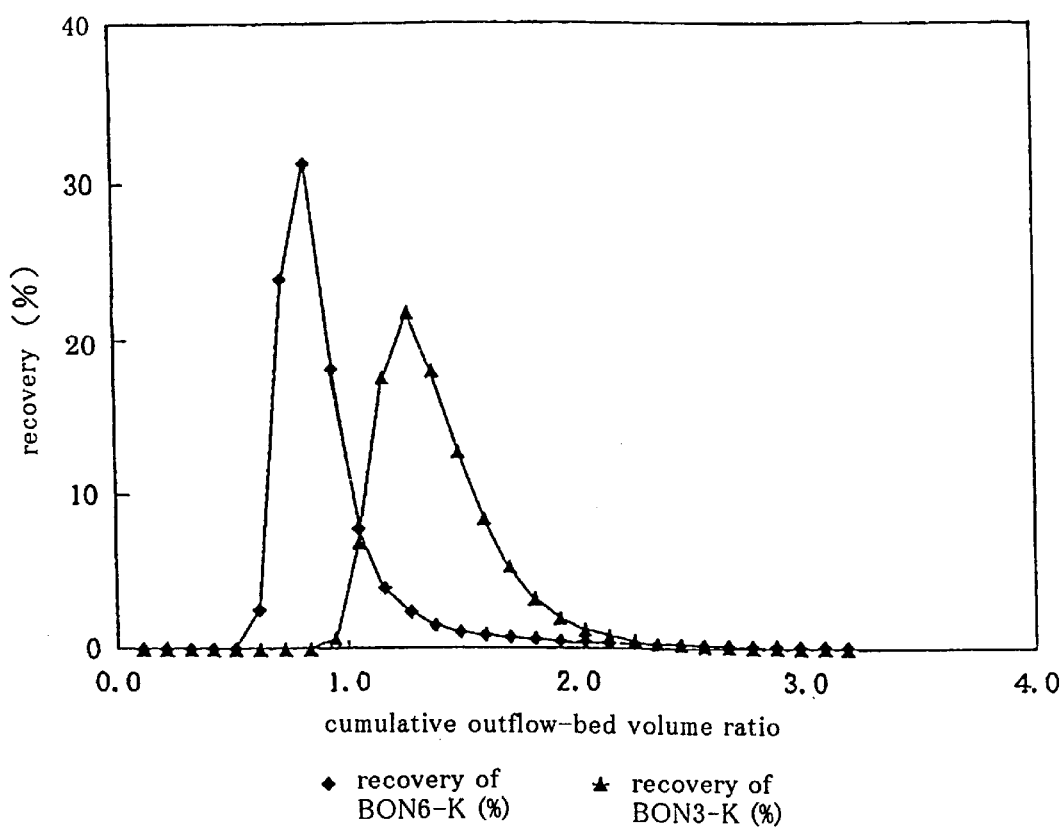
FIG. 21 is a chart showing the recoveries of BON6-K salt and BON3-K salt obtained by using 50% by weight water and 50% by weight methanol as a developer in Example 4.
Figure 22:
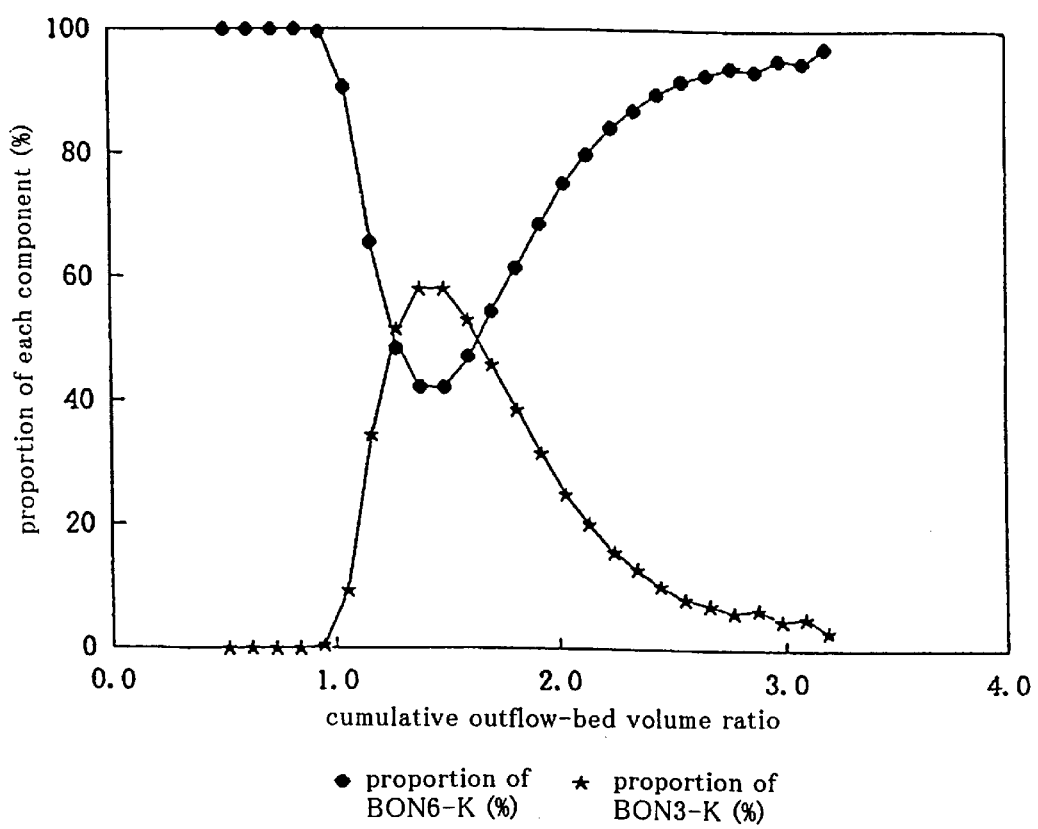
FIG. 22 is a chart showing the proportions of components, BON6-K salt and BON3-K salt, obtained by using 50% by weight water and 50% by weight methanol as a developer in Example 4.

| Methanol concentration | Correlation chart between cumulative outflow-bed volume ratio and recoveries | Correlation chart between cumulative outflow-bed volume ratio and proportions |
|---|---|---|
| 0% | FIG. 19 | FIG. 20 |
| 50% | FIG. 21 | FIG. 22 |

The results of separation and purification of BON6K and BON3-K are summarized in Table 6 on the basis of FIGS. 19–22.

TABLE 6

| Methanol concentration | Purification of BON6-K | | Purification of BON3-K | |
|---|---|---|---|---|
| | proportion (%) | recovery (%) | proportion (%) | recovery (%) |
| 0% | 100 | 77.2 | — | — |
| 50% | >99 | 75.7 | >50 | 60.9 |

EXAMPLE 5

The development was conducted as in Example 4 with the exceptions that Diaion SP207 (specific surface area: 627 $m^2/g$, pore volume (mercury press-in method): 0.79 ml/g; Mitsubishi Chemical Corp.) was used as an adsorbent.

Each fraction collected was then weighed, and measured for its BON6 and BON3 concentrations to calculate the weights of the potassium salts in the fraction, as in Example 4. The recoveries of BON6-K and BON3-K in each fraction are shown in each of FIGS. 23 and 25, and the proportions of BON6-K and BON3-K are shown in each of FIGS. 24 and 26. (The relations between methanol concentrations and Figures are shown in Table 7.)

TABLE 7

Figure 23:
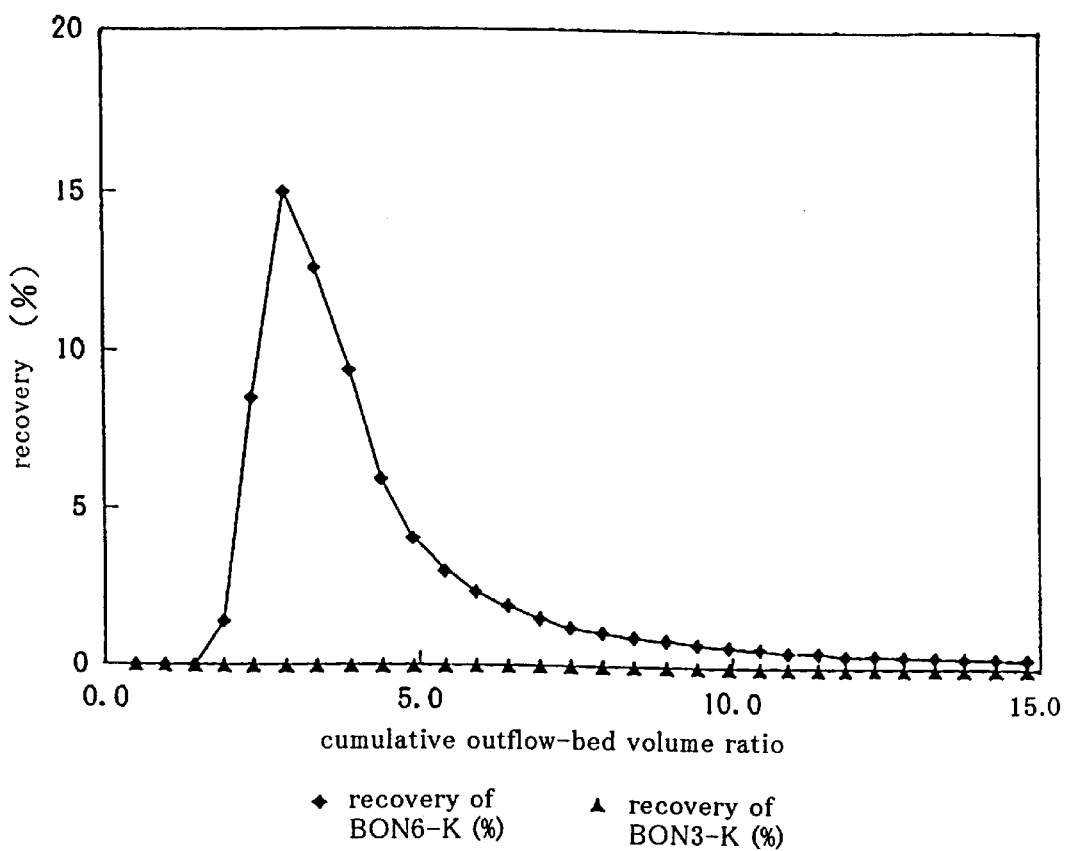
FIG. 23 is a chart showing the recoveries of BON6-K salt and BON3-K salt obtained by using water as a developer in Example 5.
Figure 24:
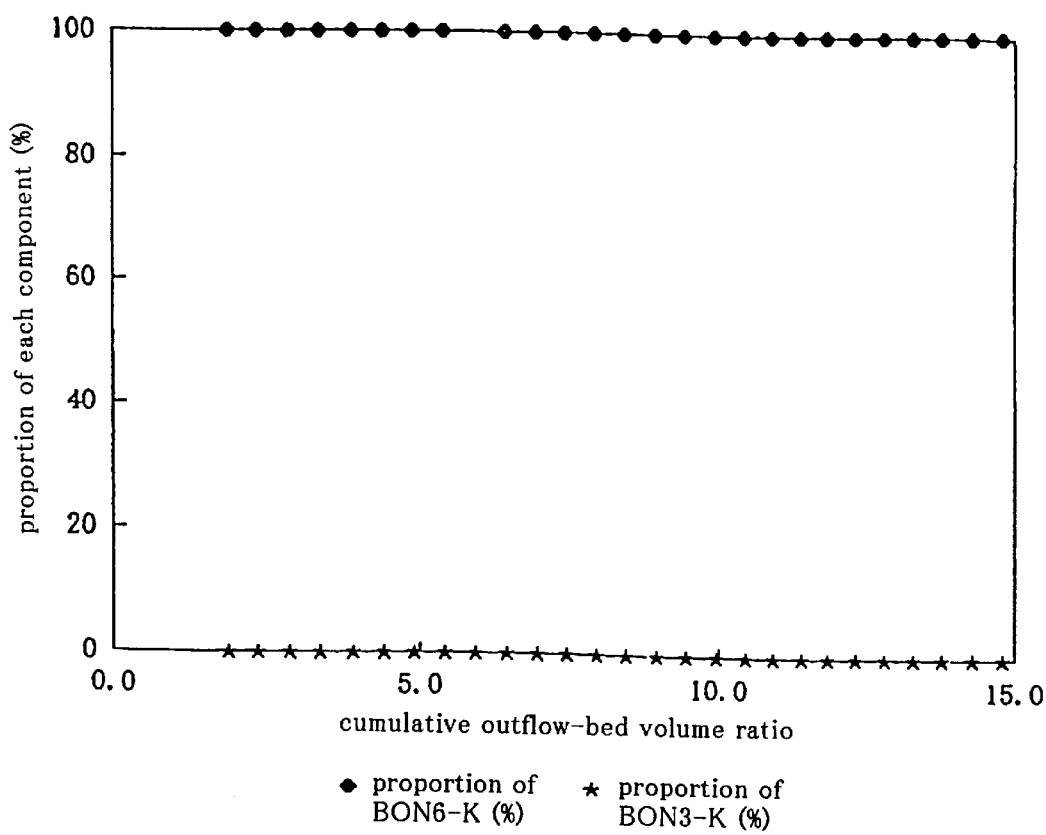
FIG. 24 is a chart showing the proportions of components, BON6-K salt and BON3-K salt, obtained by using water as a developer in Example 5.
Figure 25:
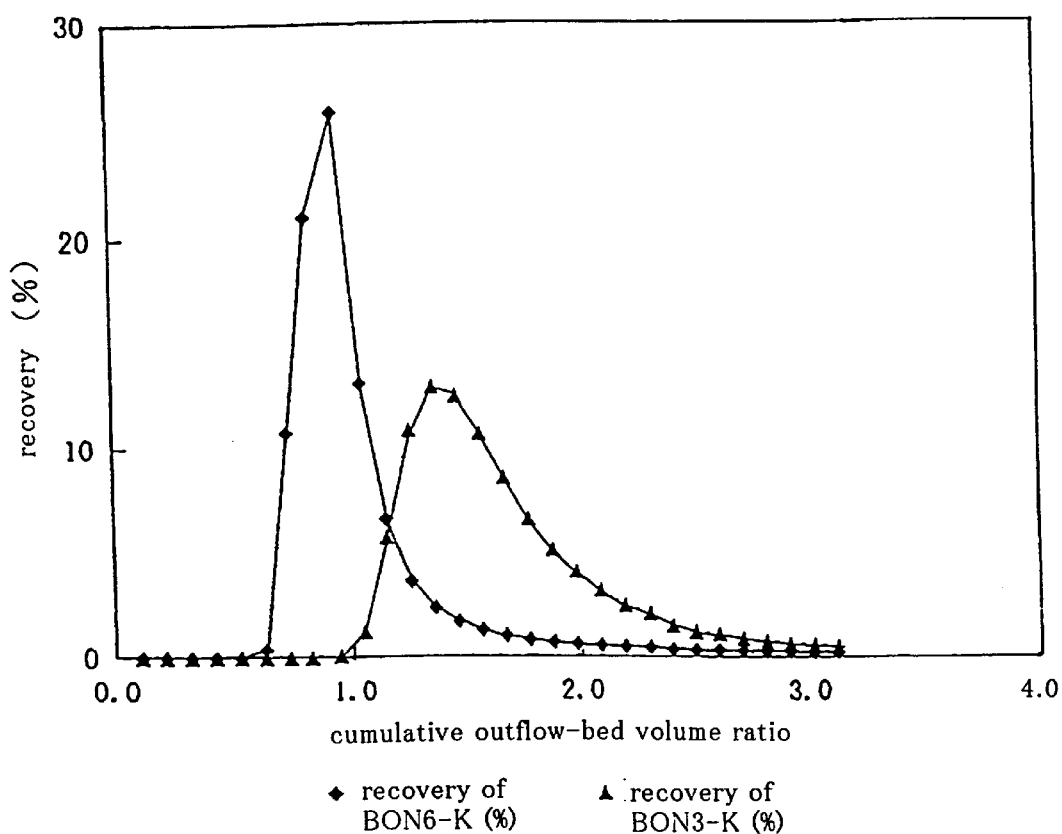
FIG. 25 is a chart showing the recoveries of BON6-K salt and BON3-K salt obtained by using 50% by weight water and 50% by weight methanol as a developer in Example 5.
Figure 26:
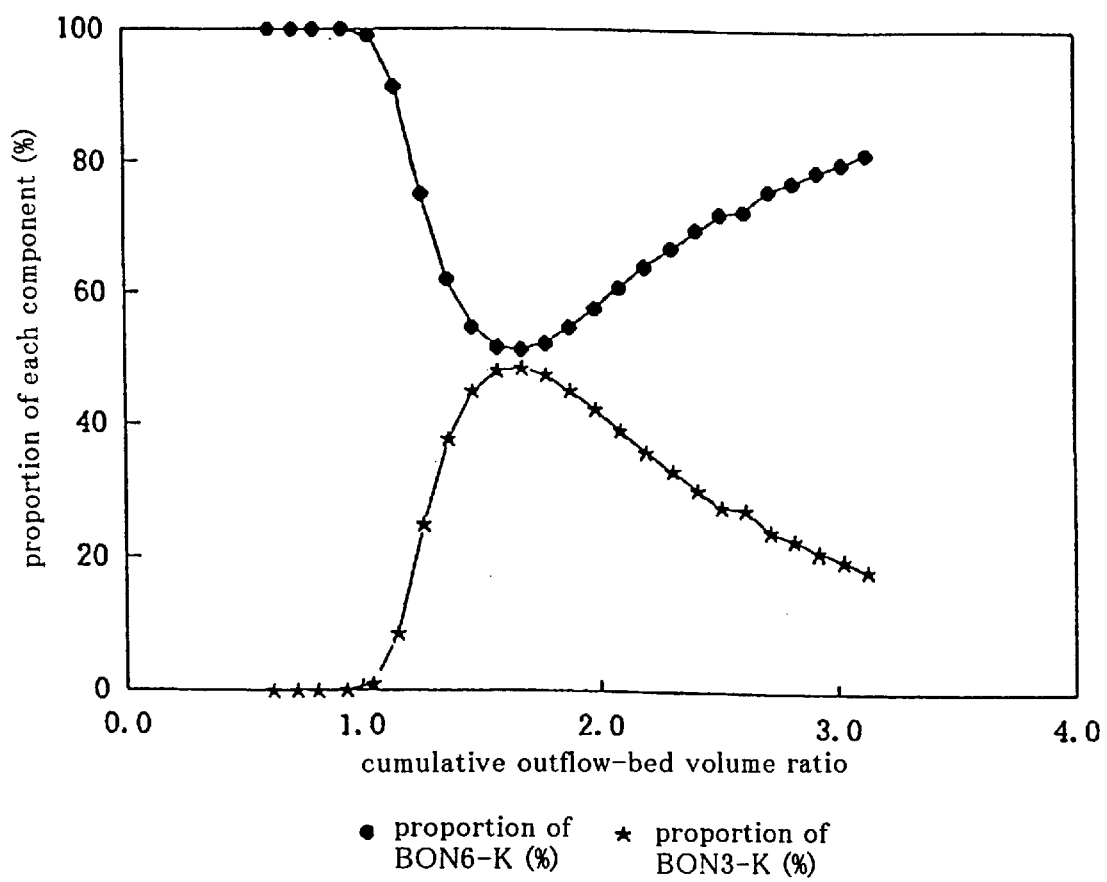
FIG. 26 is a chart showing the proportions of components, BON6-K salt and BON3-K salt, obtained by using 50% by weight water and 50% by weight methanol as a developer in Example 5.

| Methanol concentration | Correlation chart between cumulative outflow-bed volume ratio and recoveries | Correlation chart between cumulative outflow-bed volume ratio and proportions |
|---|---|---|
| 0% | FIG. 23 | FIG. 24 |
| 50% | FIG. 25 | FIG. 26 |

The results of separation and purification of BON6-K and BON3-K are summarized in Table 8 on the basis of FIGS. 23–26.

TABLE 8

| Methanol concentration | Purification of BON6-K | | Purification of BON3-K | |
|---|---|---|---|---|
| | proportion (%) | recovery (%) | proportion (%) | recovery (%) |
| 0% | 100 | 75.4 | — | — |
| 50% | >99 | 71.1 | >40 | 47.5 |

EXAMPLE 6

The development was conducted as in Example 4 with the exceptions that a nonionic porous synthetic adsorbent (Diaion HP2MG: Mitsubishi Chemical Corp.; specific surface area: 473 $m^2/g$, pore volume (mercury-compression method): 1.15 ml/g) which comprises, as the basic structure, a methacrylic copolymer mainly composed of monomethacrylate and dimethacrylate was used as an adsorbent, and that the solution outflowing from the bottom of the column was collected in about 15 ml (50% by weight methanol) or about 50 ml (0% by weight methanol) fractions.

Each fraction thus collected was then weighed, and measured for its BON6 and BON3 concentrations to calculate the weights of the potassium salts in the fraction, as in Example 4. The recoveries of BON6-K and BON3-K in each fraction are shown in each of FIGS. 27 and 29, and the proportions of BON6-K and BON3-K are shown in each of FIGS. 28 and 30. (The relations between methanol concentrations and Figures are shown in Table 9.)

TABLE 9

Figure 27:
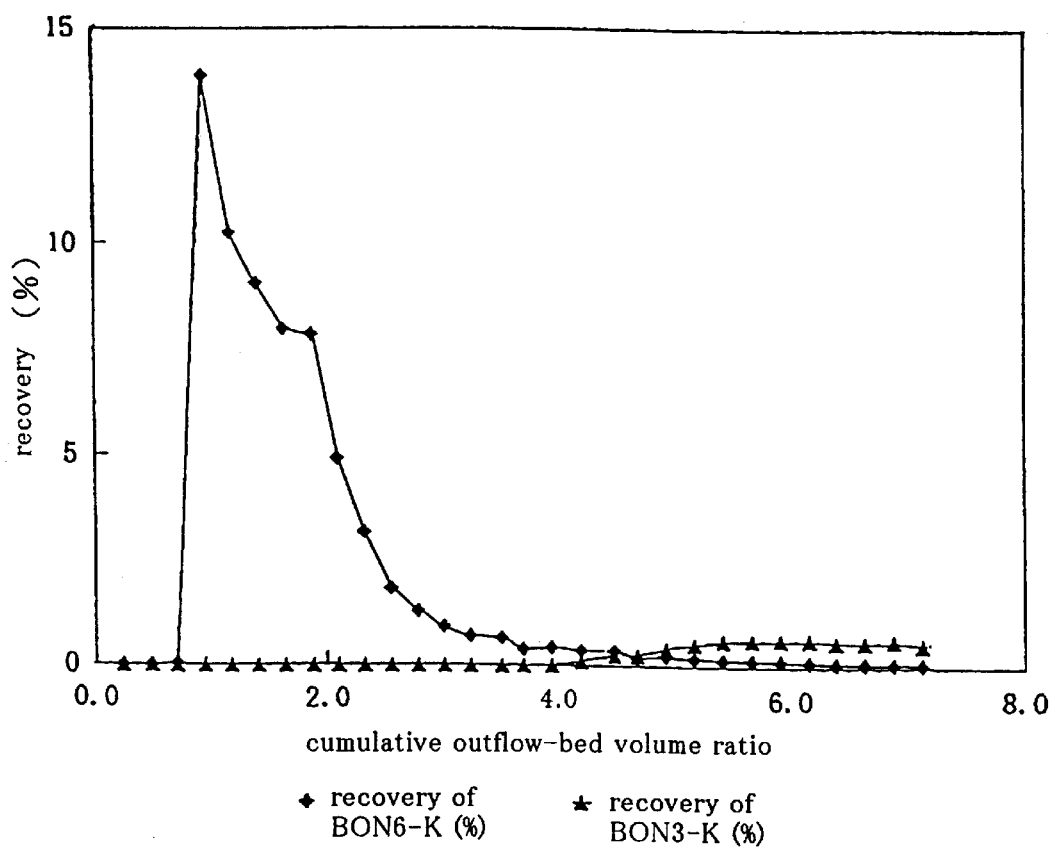
FIG. 27 is a chart showing the recoveries of BON6-K salt and BON3-K salt obtained by using water as a developer in Example 6.
Figure 28:
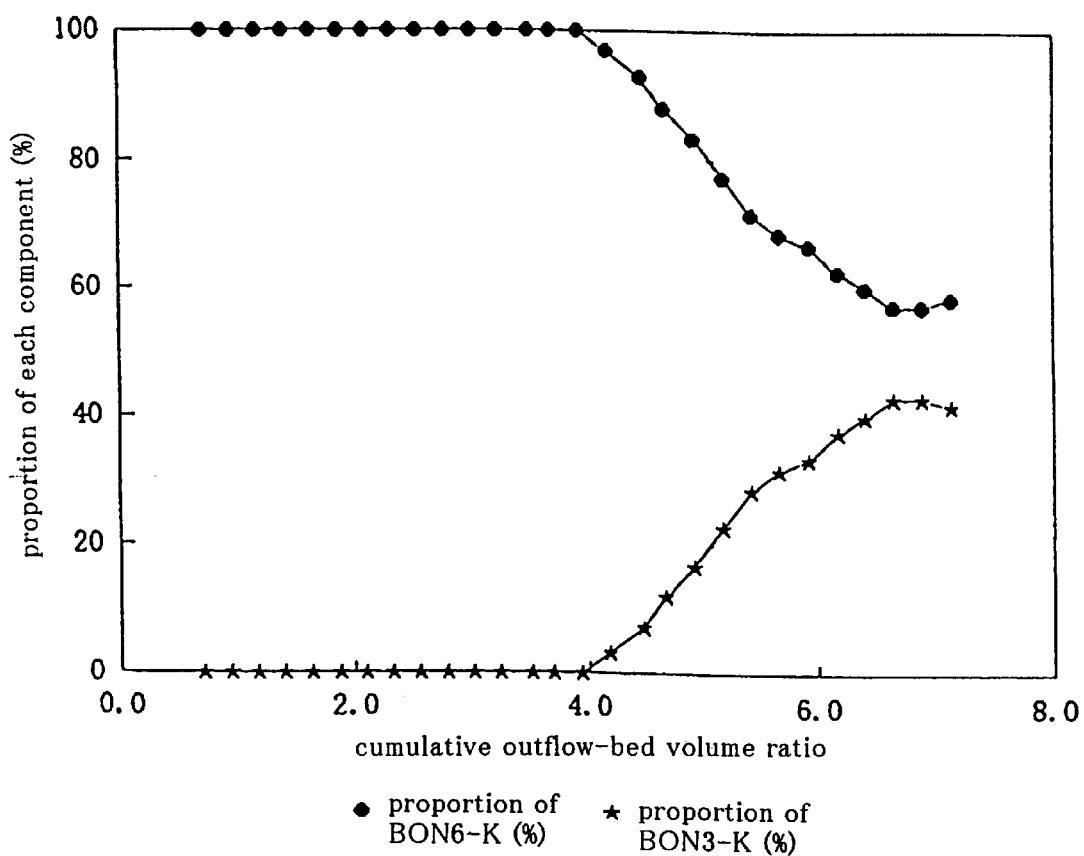
FIG. 28 is a chart showing the proportions of components, BON6-K salt and BON3-K salt, obtained by using water as a developer in Example 6.
Figure 29:
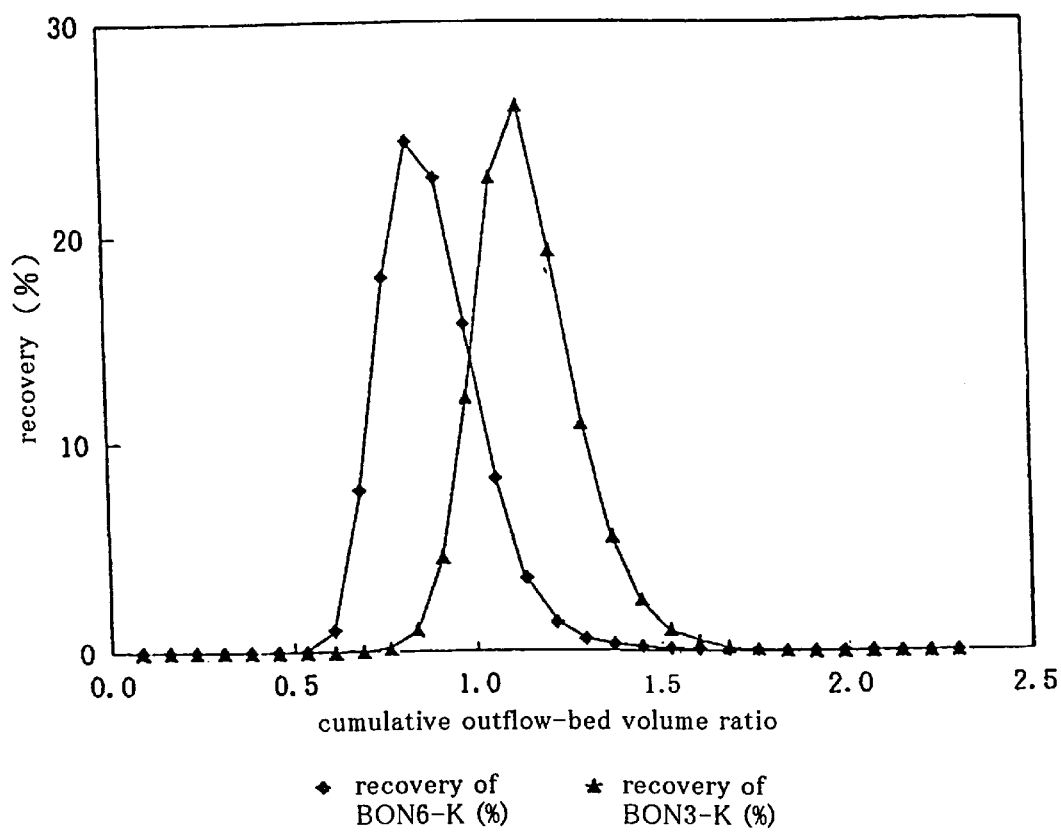
FIG. 29 is a chart showing the recoveries of BON6-K salt and BON3-K salt obtained by using 50% by weight water and 50% by weight methanol as a developer in Example 6.
Figure 30:
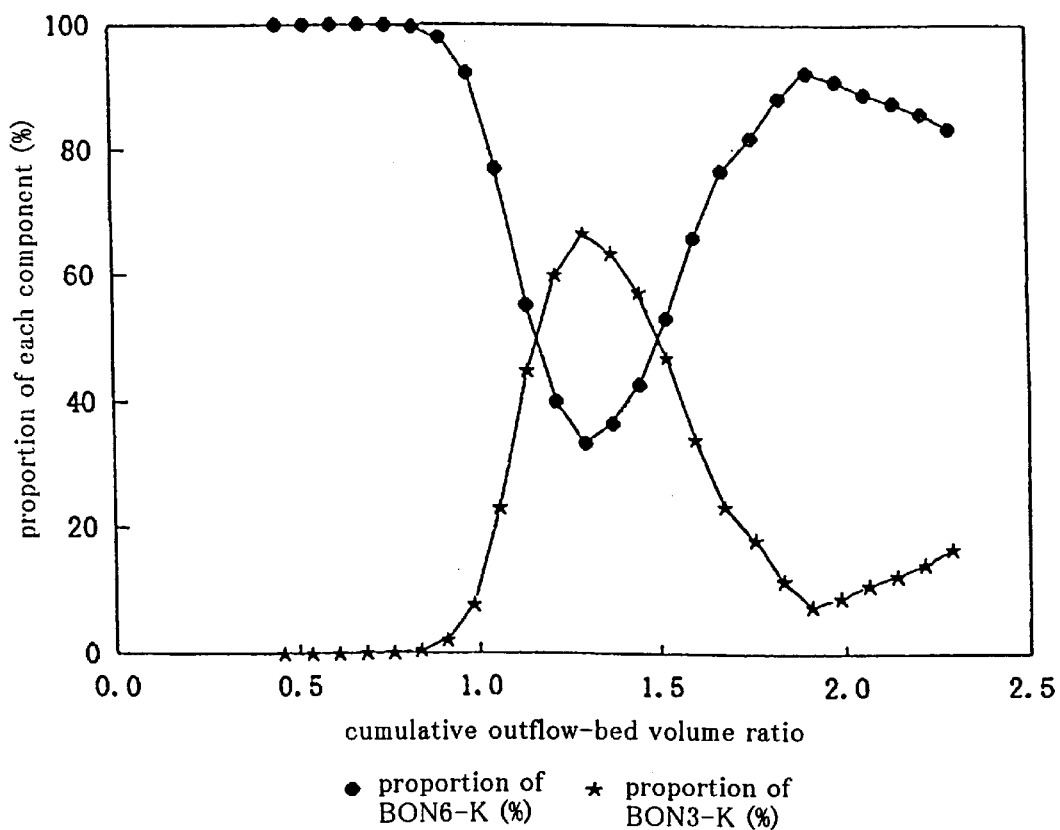
FIG. 30 is a chart showing the proportions of components, BON6-K salt and BON3-K salt, obtained by using 50% by weight water and 50% by weight methanol as a developer in Example 6.

| Methanol concentration | Correlation chart between cumulative outflow-bed volume ratio and recoveries | Correlation chart between cumulative outflow-bed volume ratio and proportions |
|---|---|---|
| 0% | FIG. 27 | FIG. 28 |
| 50% | FIG. 29 | FIG. 30 |

The results of separation and purification of BON6-K and BON3-K are summarized in Table 10 on the basis of FIGS. 27–30.

TABLE 10

| Methanol concentration | Purification of BON6-K | | Purification of BON3-K | |
|---|---|---|---|---|
| | proportion (%) | recovery (%) | proportion (%) | recovery (%) |
| 0% | 100 | 63.4 | >40 | 2.3 |
| 50% | >99 | 51.2 | >60 | 35.7 |

Reference Example 1

The development was conducted as in Example 1 with the exceptions that silica gel (WAKOGEL C-200: Wako Pure Chemical Industries, Inc.) was used as an adsorbent, that the methanol concentration of 0% by weight (ion-exchanged water) was used for the developer, and that the solution outflowing from the bottom of the column was collected in about 30 ml fractions.

Figure 31:
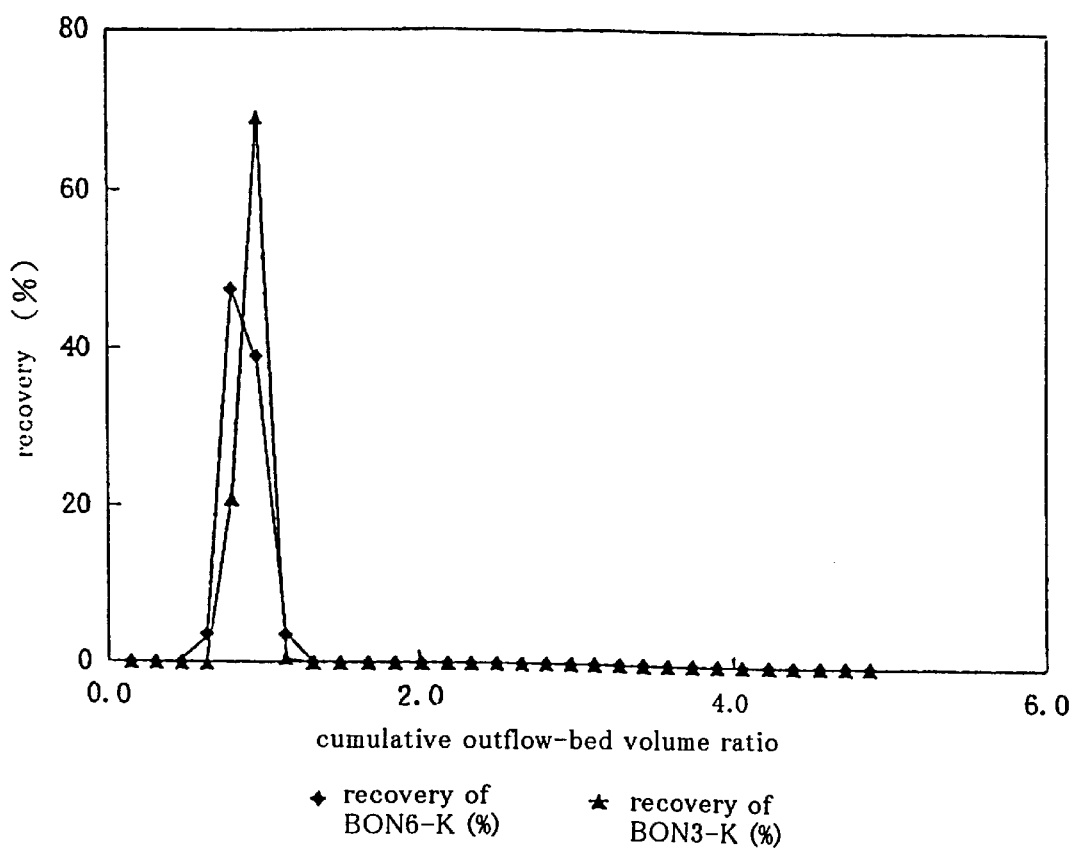
FIG. 31 is a chart showing the recoveries of BON6-K salt and BON3-K salt obtained by using water as a developer in Reference Example 1 (adsorbent: silica gel).
Figure 32:
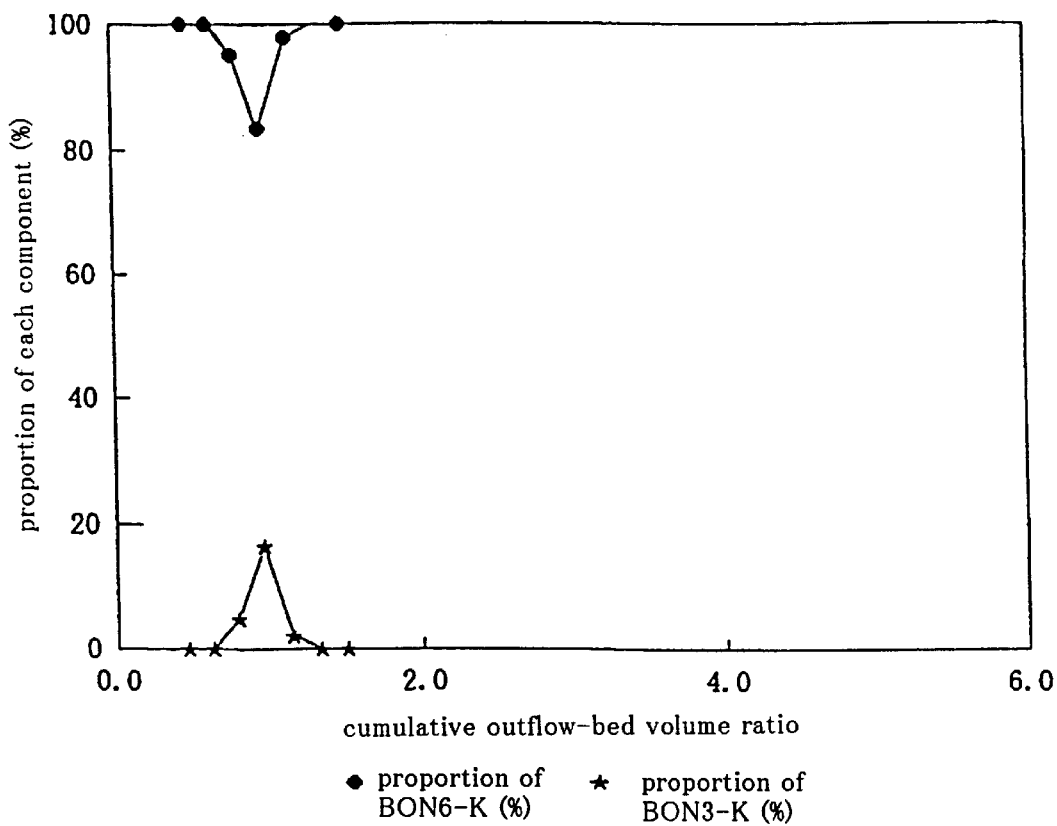
FIG. 32 is a chart showing the proportions of components, BON6-K salt and BON3-K salt, obtained by using water as a developer in Reference Example 1 (adsorbent: silica gel).

Each fraction thus collected was then weighed, and measured for its BON6 and BON3 concentrations to calculate the weights of the potassium salts in the fraction, as in Example 1. The recoveries of BON6-K and BON3-K in each fraction are each shown in FIG. 31, and the proportions of BON6-K and BON3-K are each shown in FIG. 32. BON6-K and BON3-K were, however, detected in each fraction at their original proportions, indicating that they were not adsorbed and all the input flowed through the column.

Reference Example 2

The development was conducted as in Reference Example 1 with the exceptions that activated carbon (chromatography grade: Wako Pure Chemical Industries, Inc.) was used as an adsorbent, and that the solution outflowing from the bottom of the column was collected in about 100 ml fractions.

Although each fraction thus collected was then weighed, and measured for its BON6 and BON3 concentrations as in Reference Example 1, BON6 and BON3 could not be detected in any fractions, indicating that they remained adsorbed.

Reference Example 3

The development was conducted as in Reference Example 1 with the exceptions that a polyamide (Polyamide C-100: Wako Pure Chemical Industries, Inc.) was used as an adsorbent, that 3.0 ml of the stock solution (the weight of 3.0 ml of the stock solution being separately measured) was precisely measured out, injected into the top of the above-described column bed, and then developed at room temperature with a developer at 3.0 ml/min, and that the developer outflowing from the bottom of the column was collected in about 45 ml fractions. Although each fraction thus collected was then weighed, and measured for its BON6 and BON3 concentrations as in Reference Example 1, BON6 and BON3 could not be detected in any fractions, indicating that they remained adsorbed.

Reference Example 4

The development was conducted as in Reference Example 1 with the exceptions that a cation exchange resin (Diaion PK216K (Mitsubishi Chemical Corp.) or Diaion SKI 104K (Mitsubishi Chemical Corp.)) was used as an adsorbent, and that the solution outflowing from the bottom of the column was collected in about 15 ml fractions.

Each fraction thus collected was then weighed, and measured for its BON6 and BON3 concentrations to calculate the weights of the potassium salts in the fraction, as in Reference Example 1. The recoveries of BON6-K and BON3-K in each fraction are shown in each of FIGS. 33 and 35, and the proportions of BON6-K and BON3-K are shown in each of FIGS. 34 and 36. BON6-K and BON3-K were, however, detected in each fraction at their original proportions, indicating that they were not adsorbed and all the input flowed through the column. (The relations between ion-exchange resins and Figures are shown in Table 11.)

TABLE 11

Figure 33:
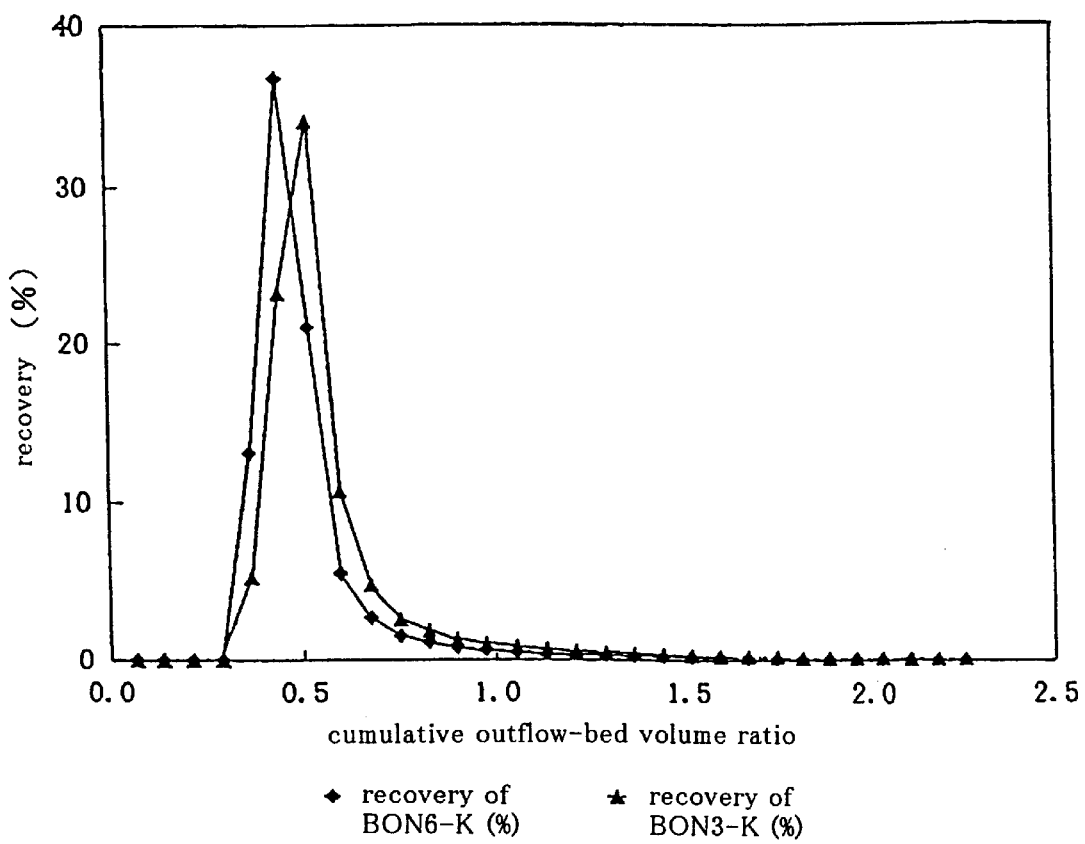
FIG. 33 is a chart showing the recoveries of BON6-K salt and BON3-K salt obtained by using water as a developer in Reference Example 4 (adsorbent: a cation exchange resin).
Figure 34:
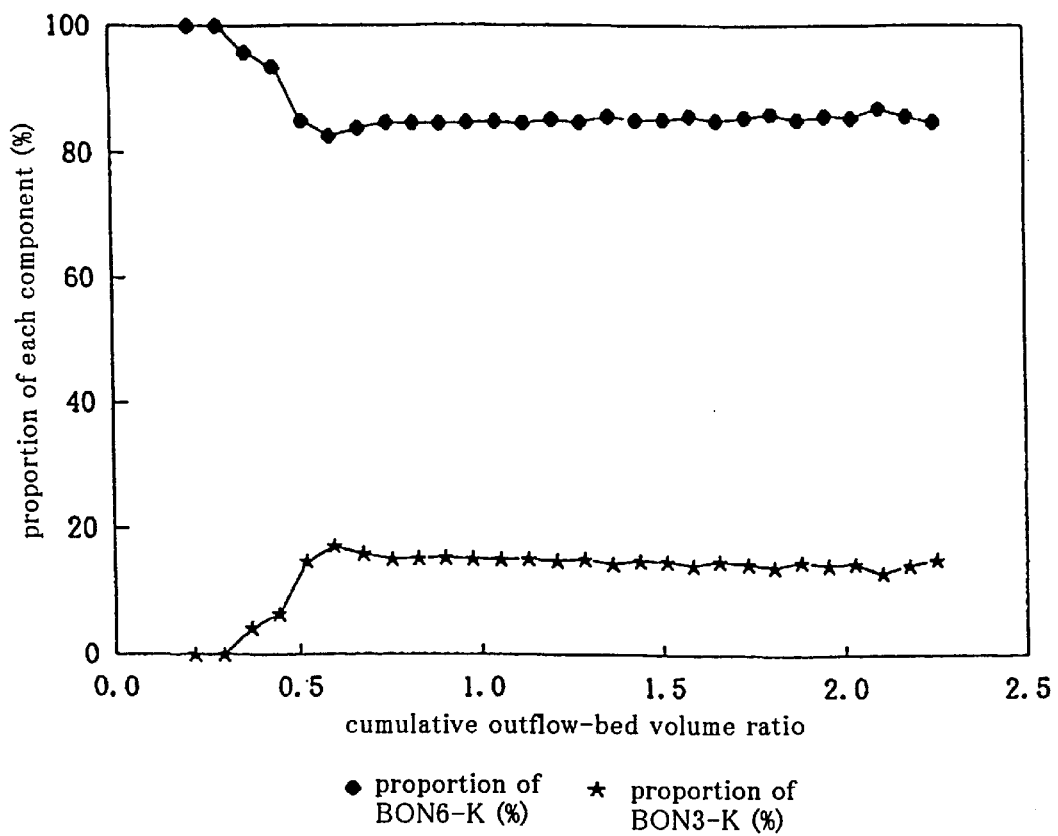
FIG. 34 is a chart showing the proportions of components, BON6-K salt and BON3-K salt, obtained by using water as a developer in Reference Example 4 (adsorbent: a cation exchange resin).
Figure 35:
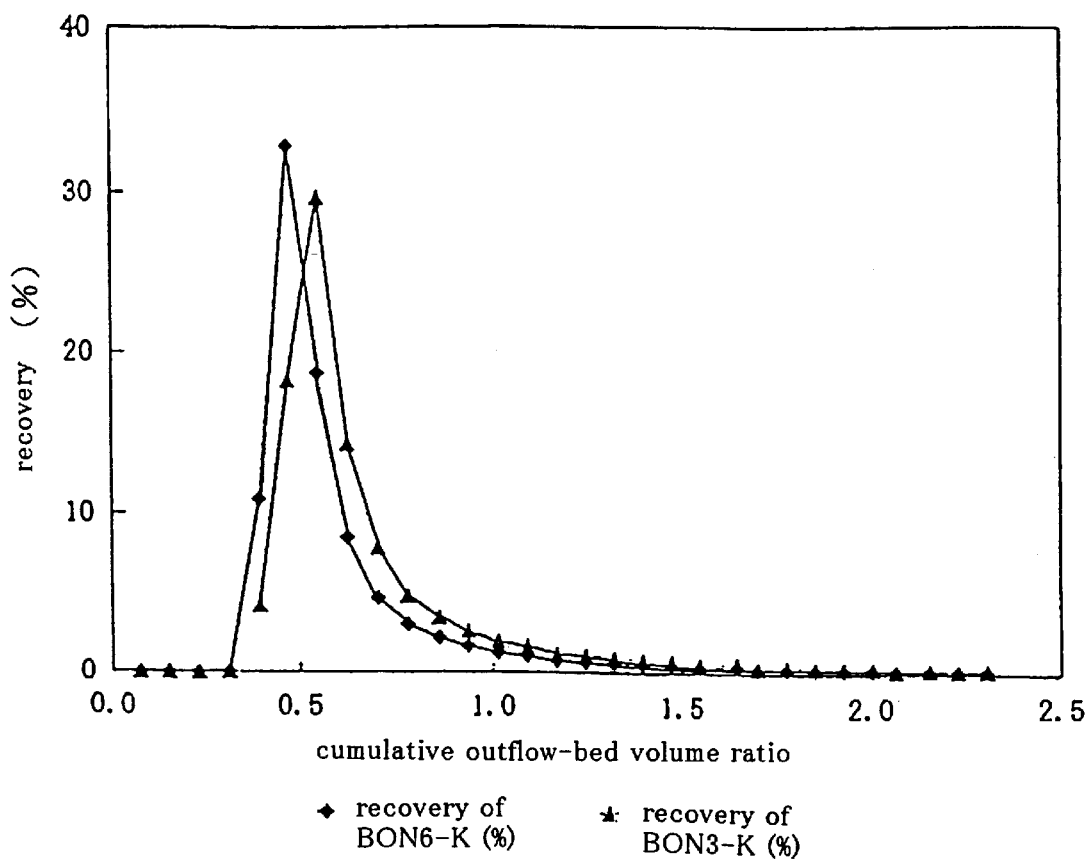
FIG. 35 is a chart showing the recoveries of BON6-K salt and BON3-K salt obtained by using water as a developer in Reference Example 4 (adsorbent: a cation exchange resin).
Figure 36:
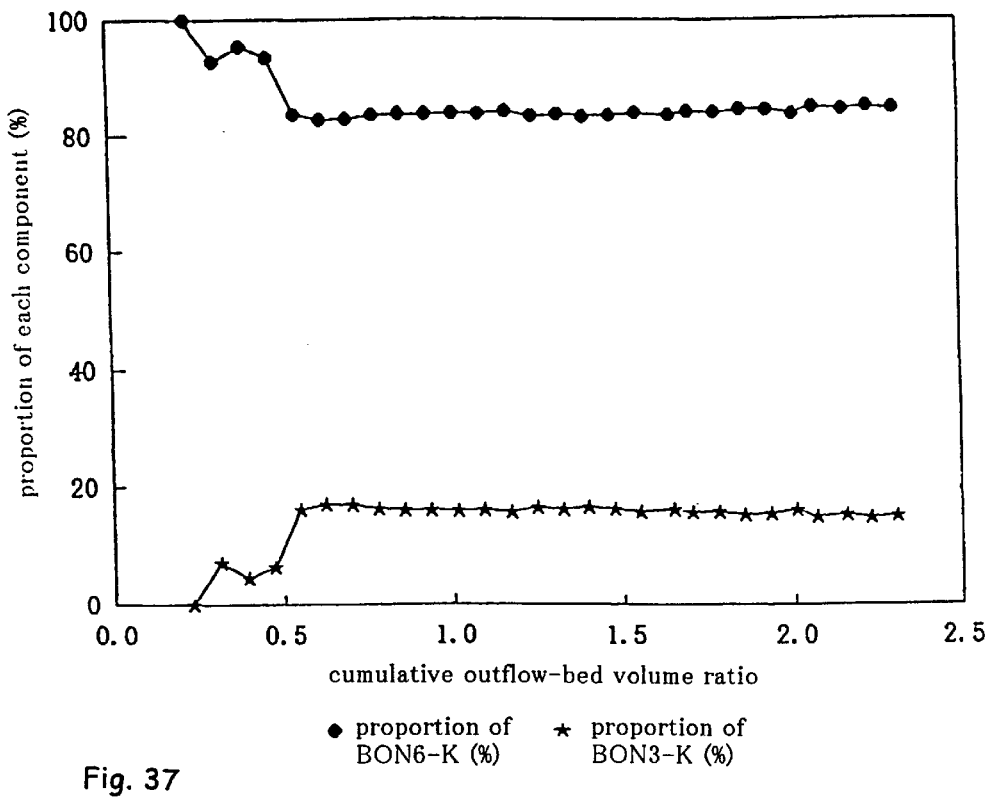
FIG. 36 is a chart showing the proportions of components, BON6K salt and BON3-K salt, obtained by using water as a developer in Reference Example 4 (adsorbent: a cation exchange resin).

| Ion-exchange resin | Correlation chart between cumulative outflow-bed volume ratio and recoveries | Correlation chart between cumulative outflow-bed volume ratio and proportions |
|---|---|---|
| PK216K | FIG. 33 | FIG. 34 |
| SK104K | FIG. 35 | FIG. 36 |

Reference Example 5

The development was conducted as in Reference Example 1 with the exceptions that an anion exchange resin (Diaion WA10C1 (Mitsubishi Chemical Corp.) or Diaion WA20C1 (Mitsubishi Chemical Corp.)) was used as an adsorbent, and that the solution outflowing from the bottom of the column was collected in about 50 ml fractions.

Although each fraction thus collected was then weighed, and measured for its BON6 and BON3 concentrations as in Reference Example 1, BON6 and BON3 could not be detected in any fractions, indicating that they remained adsorbed.

EXAMPLE 7

The development was conducted as in Example 4 with the exceptions that Diaion SP207 or Diaion HP2MG was used as an adsorbent, that the stock solution was prepared by dissolving 5.0 g of BON6-K, 5.0 g of BON3-K, and 5.0 g of 2-hydroxynaphthalene-3,6-dicarboxylic acid dipotassium salt (hereinafter referred to as BON3,6-K2) in the developer (ion-exchanged water), and that the solution outflowing from the bottom of the column was collected in about 30 ml (Diaion SP207) or about 20 ml (Diaion HP2MG) fractions.

Each fraction thus collected was then weighed, and measured for its BON6, BON3, and BON3,6 concentrations to calculate the weighs of each potassium salts in the fraction, as in Example 4. The recoveries of BON6K, BON3-K, and BON3, 6-K2 in each fraction are each shown in FIGS. 37 and 39, and the proportions of BON6K, BON3-K, and BON3,6-K2 are shown in each of FIGS. 38 and 40 (the relations between adsorbents and Figures are shown in Table 12).

Recovery of BON3,6-K2 (%)=100×(the weight of BON3, 6-K2 in the fraction)/(the weight of BON3,6-K2 in the raw material)

Proportion of BON6K (%)=100×(the weight of BON6-K in the fraction)/(the total weight of BON6-K, BON3-K, and BON3,-K2 in the fraction)

Proportion of BON3-K (%)=100 ×(the weight of BON3-K in the fraction)/(the total weight of BON6-K BON3-K, and BON3,6-K2 in the fraction)

Proportion of BON3,6-K2 (%)=100×(the weight of BON3,6-K2 in the fraction)/(the total weight of BON6-K, BON3-K, and BON3,6-K2 in the fraction)

TABLE 12

Figure 37:
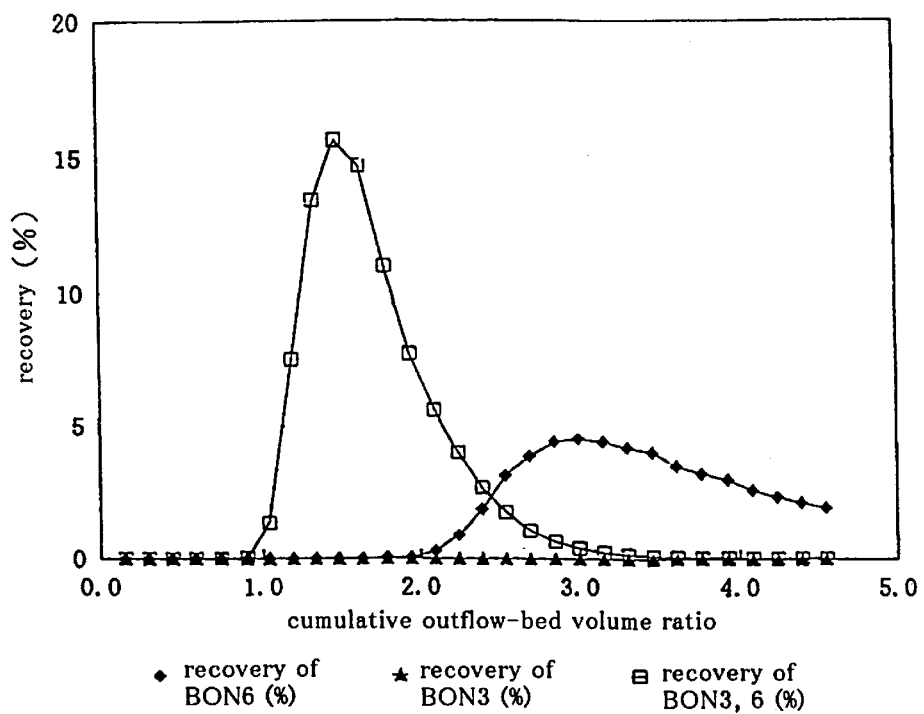
FIG. 37 is a chart showing the recoveries of BON6-K salt, BON3-K salt, and BON3,6-K2 salt obtained by using water as a developer in Example 7 (adsorbent: Diaion SP207).
Figure 38:
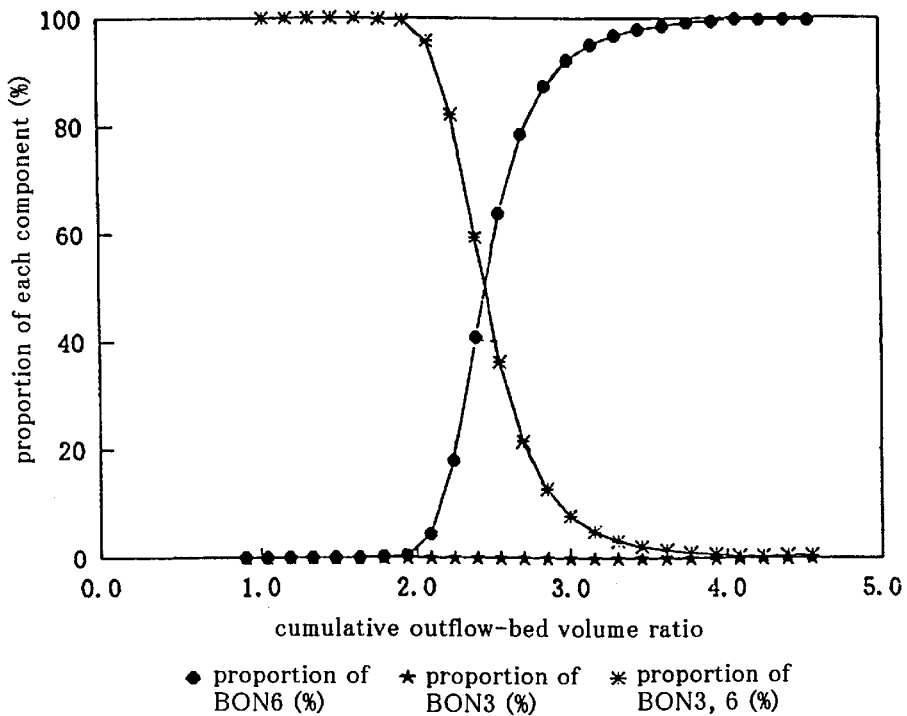
FIG. 38 is a chart showing the proportions of components, BON6-K salt, BON3-K salt, and BON3,6-K2 salt, obtained by using water as a developer in Example 7 (adsorbent: Diaion SP207).
Figure 39:
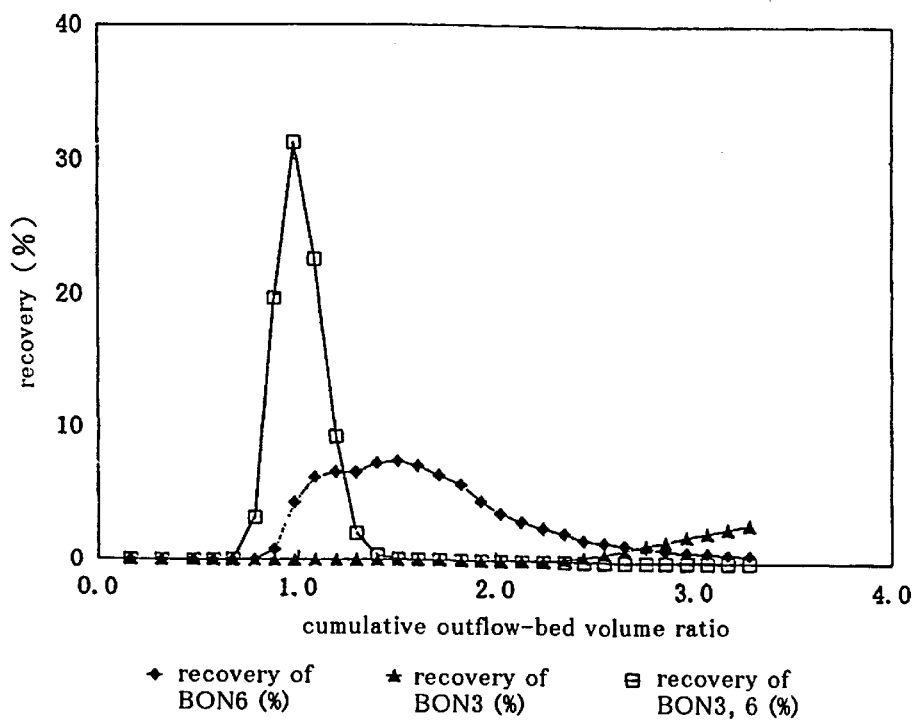
FIG. 39 is a chart showing the recoveries of BON6-K salt, BON3-K salt, and BON3,6-K2 salt obtained by using water as a developer in Example 7 (adsorbent: Diaion HP2MG).
Figure 40:
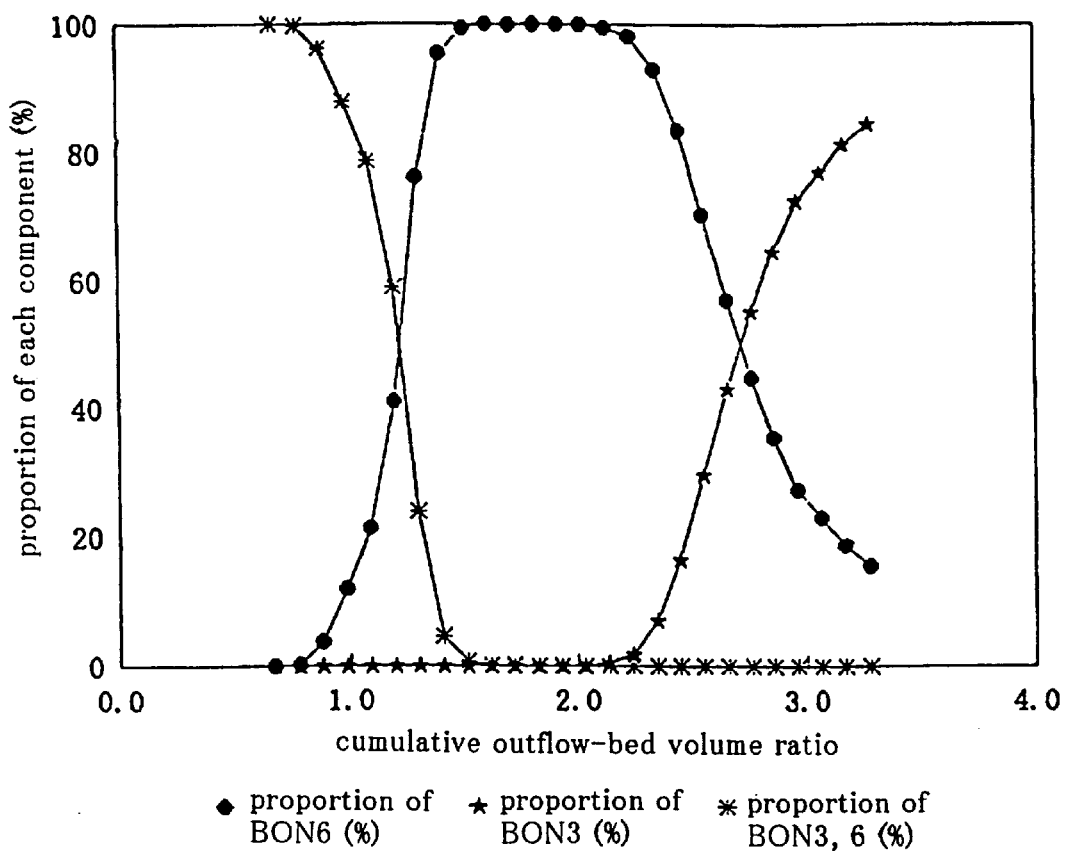
FIG. 40 is a chart showing the proportions of components, BON6-K salt, BON3-K salt, and BON3,6K2 salt, obtained by using water as a developer in Example 7 (adsorbent: Diaion HP2MG).

| Adsorbent | Correlation chart between cumulative outflow-bed volume ratio and recoveries | Correlation chart between cumulative outflow-bed volume ratio and proportions |
|---|---|---|
| SP207 | FIG. 37 | FIG. 38 |
| HP2MG | FIG. 39 | FIG. 40 |

The results of separation and purification of BON6-K, BON3-K, and BON3,6-K2 are summarized in Table 13 on the basis of FIGS. 37–40.

TABLE 13

| Adsorbent | Purification of BON6-K | | Purification of BON3-K | | Purification of BON3, 6-K2 | |
|---|---|---|---|---|---|---|
| | proportion (%) | recovery (%) | proportion (%) | recovery (%) | proportion (%) | recovery (%) |
| SP207 | >95 | 29.8 | — | — | >95 | 77.0 |
| HP2MG | >93 | 47.5 | >85 | 2.8 | >88 | 54.2 |

Industrial Applicability

The process of the present invention enables separation and purification of intended alkali metal salt(s) of hydroxynaphthalenecarboxylic acid(s) at high accuracy and at high yield from a mixture of alkali metal salts of hydroxynaphthalenecarboxyiic acids, such as those obtained in Kolbe-Schmitt process, without neutralizing them completely, and thereby improves the productivity of such industrial processes.

What is claimed is:

1. A process for separating and purifying alkali metal salts of hydroxynaphthalenecarboxylic acids, characterized in that a mixture of alkali metal salts of hydroxynaphthalenecarboxylic acids is adsorbed to a nonionic porous synthetic adsorbent, and treated with water or water and water-soluble organic solvent(s).

2. A process for separating and purifying alkali metal salts of hydroxynaphthalenecarboxylic acids of claim 1, in which the nonionic porous synthetic adsorbent is an aromatic copolymer mainly composed of styrene and divinylbenzene or a methacrylic copolymer mainly composed of monomethacrylate and dimethacrylate.

3. A process for separating and purifying alkali metal salts of hydroxynaphthalenecarboxylic acids of claim 1, in which the mixture of alkali metal salts of hydroxynaphthalenecarboxylic acids contains the alkali metal salt of 2-hydroxynaphthalene-3-carboxylic acid and the alkali metal salt of 2-hydroxynaphthalene-6-carboxylic acid.

4. A process for separating and purifying alkali metal salts of hydroxynaphthalenecarboxylic acids of claim 1, in which the alkali metal salts of hydroxynaphthalenecarboxylic acids are such salts in the form of carboxylates.

5. A process for separating and purifying alkali metal salts of hydroxynaphthalenecarboxylic acids of claim 1, in which the mixture of alkali metal salts of hydroxynaphthalenecarboxylic acids is dissolved in water or water and water-soluble organic solvent(s), injected into the top of an column packed with a nonionic porous synthetic adsorbent, developed firstly with water or water-soluble organic solvent(s) having a high water content and then with increased proportion(s) of water-soluble organic solvent(s) in the developer.

* * * * *

UNITED STATES PATENT AND TRADEMARK OFFICE
CERTIFICATE OF CORRECTION

PATENT NO. : 6,194,608 B1
DATED : February 27, 2001
INVENTOR(S) : Ryuzo Ueno, Masaya Kitayama, Kuniyo Yanagawase, Yoshiro Uchiyama, Shigeji Mori It is certified that error appears in the above-identified patent and that said Letters Patent is hereby corrected as shown below:

<u>Title page,</u>
Item [73] Assignee please delete "Veno" and insert -- Ueno --.

Signed and Sealed this

Twenty-third Day of October, 2001

Attest:

*Nicholas P. Godici*

NICHOLAS P. GODICI
*Attesting Officer*     *Acting Director of the United States Patent and Trademark Office*